US008496943B2

(12) United States Patent
Fereira et al.

(10) Patent No.: US 8,496,943 B2
(45) Date of Patent: Jul. 30, 2013

(54) NON-AQUEOUS SINGLE PHASE VEHICLES AND FORMULATIONS UTILIZING SUCH VEHICLES

(75) Inventors: Pamela J. Fereira, Santa Clara, CA (US); Michael A. Desjardin, Sunnyvale, CA (US); Catherine M. Rohloff, Los Altos, CA (US); Stephen A. Berry, Hollister, CA (US); Ekaterina S. Zlatkova-Karaslavova, San Jose, CA (US)

(73) Assignee: Durect Corporation, Cupertino, CA (US)

( * ) Notice: Subject to any disclaimer, the term of this patent is extended or adjusted under 35 U.S.C. 154(b) by 1852 days.

(21) Appl. No.: 11/183,477

(22) Filed: Jul. 18, 2005

(65) Prior Publication Data

US 2005/0276856 A1    Dec. 15, 2005

Related U.S. Application Data

(63) Continuation-in-part of application No. 10/814,826, filed on Mar. 31, 2004.

(60) Provisional application No. 60/459,300, filed on Mar. 31, 2003, provisional application No. 60/650,252, filed on Feb. 3, 2005.

(51) Int. Cl.
*A61K 9/00* (2006.01)

(52) U.S. Cl.
USPC ................ 424/400; 424/486; 424/489

(58) Field of Classification Search
USPC .......................... 424/400, 486, 489
See application file for complete search history.

(56) References Cited

U.S. PATENT DOCUMENTS

| 3,797,492 A | | 3/1974 | Place ............................ 128/260 |
| 3,987,790 A | | 10/1976 | Eckenhoff et al. ............ 128/260 |
| 4,008,719 A | | 2/1977 | Theeuwes et al. ............ 128/260 |
| 4,069,251 A | * | 1/1978 | Mannsfeld et al. ............ 562/559 |
| 4,305,927 A | | 12/1981 | Theeuwes et al. .............. 424/15 |
| 4,562,024 A | * | 12/1985 | Rogerson ..................... 264/117 |
| 4,782,104 A | * | 11/1988 | Nakanishi ..................... 524/157 |
| 4,865,845 A | | 9/1989 | Eckenhoff et al. ............ 424/424 |
| 4,874,388 A | | 10/1989 | Wong et al. ................. 604/891.1 |
| 5,034,229 A | | 7/1991 | Magruder et al. ............ 424/422 |
| 5,057,318 A | | 10/1991 | Magruder et al. ............ 424/438 |
| 5,059,423 A | | 10/1991 | Magruder et al. ............ 424/438 |

(Continued)

FOREIGN PATENT DOCUMENTS

| WO | WO 98/27962 | 7/1998 |
| WO | WO 99/33446 | 7/1999 |

(Continued)

OTHER PUBLICATIONS

Kim et al, "Comparing the effect on protein stability of methionine oxidation versus mutagenesis: steps toward engineering oxidative resistance in proteins," Protein Engineering, vol. 14, No. 5, pp. 343-347, 2001.*

(Continued)

*Primary Examiner* — Rachael E Bredefeld
(74) *Attorney, Agent, or Firm* — Steven J. Helmer

(57) ABSTRACT

The present invention is related to materials and methods for forming polymeric delivery vehicles that reduces risk of oxidative degradation of a carried drug and the resulting compositions.

19 Claims, 14 Drawing Sheets

U.S. PATENT DOCUMENTS

| | | | |
|---|---|---|---|
| 5,110,596 A | 5/1992 | Magruder et al. | 424/438 |
| 5,112,614 A | 5/1992 | Magruder et al. | 424/422 |
| 5,137,727 A | 8/1992 | Eckenhoff | 424/422 |
| 5,151,093 A | 9/1992 | Theeuwes et al. | 604/892.1 |
| 5,219,572 A | 6/1993 | Sivaramakrishnan et al. | 424/438 |
| 5,234,692 A | 8/1993 | Magruder et al. | 424/473 |
| 5,234,693 A | 8/1993 | Magruder et al. | 424/473 |
| 5,279,608 A | 1/1994 | Cherif Cheikh | 604/892.1 |
| 5,308,348 A | 5/1994 | Balaban et al. | 604/892.1 |
| 5,312,389 A | 5/1994 | Theeuwes et al. | 604/892.1 |
| 5,336,057 A | 8/1994 | Fukuda et al. | 417/395 |
| 5,368,588 A | 11/1994 | Bettinger | 604/891.1 |
| 5,511,355 A | 4/1996 | Dingler | 52/729.5 |
| 5,557,318 A | 9/1996 | Gabriel | 348/7 |
| 5,713,847 A | 2/1998 | Howard, III et al. | |
| 5,728,396 A | 3/1998 | Peery et al. | 424/422 |
| 5,836,935 A | 11/1998 | Ashton et al. | 604/891.1 |
| 5,874,388 A | 2/1999 | Hsu | 508/183 |
| 5,976,109 A | 11/1999 | Heruth | 604/140 |
| 5,985,305 A | 11/1999 | Peery et al. | 424/422 |
| 5,997,527 A | 12/1999 | Gumucio et al. | 604/892.1 |
| 5,997,902 A | 12/1999 | Maruyama et al. | 424/473 |
| 6,093,420 A * | 7/2000 | Baichwal | 424/468 |
| 6,113,938 A | 9/2000 | Chen et al. | 424/423 |
| 6,132,420 A | 10/2000 | Dionne et al. | 604/892.1 |
| 6,156,331 A | 12/2000 | Peery et al. | 424/422 |
| 6,217,906 B1 | 4/2001 | Gumucio et al. | 424/473 |
| 6,261,584 B1 | 7/2001 | Peery et al. | 424/422 |
| 6,270,787 B1 | 8/2001 | Ayer | 424/423 |
| 6,283,949 B1 | 9/2001 | Roorda | 604/288.02 |
| 6,375,978 B1 | 4/2002 | Kleiner et al. | 424/449 |
| 6,395,292 B2 | 5/2002 | Peery et al. | 424/422 |
| 6,508,808 B1 | 1/2003 | Carr et al. | 604/892.1 |
| 6,525,102 B1 * | 2/2003 | Chen et al. | 424/85.2 |
| 6,840,931 B2 | 1/2005 | Peterson et al. | 604/892.1 |
| 2003/0021841 A1 * | 1/2003 | Matharu et al. | 424/465 |
| 2003/0044467 A1 | 3/2003 | Brodbeck et al. | 424/486 |
| 2003/0059376 A1 | 3/2003 | Libbey, III et al. | 424/46 |
| 2003/0114430 A1 * | 6/2003 | MacLeod et al. | 514/177 |
| 2003/0180364 A1 | 9/2003 | Chen et al. | 424/486 |
| 2003/0215515 A1 | 11/2003 | Truon-le et al. | 424/489 |
| 2005/0008661 A1 | 1/2005 | Fereira et al. | 424/400 |
| 2005/0095284 A1 | 5/2005 | Trautman | 424/451 |
| 2005/0276856 A1 | 12/2005 | Fereira et al. | 424/486 |

FOREIGN PATENT DOCUMENTS

| | | |
|---|---|---|
| WO | WO 00/45790 | 8/2000 |
| WO | WO 00/54745 A2 | 9/2000 |
| WO | WO 01/43528 A2 | 12/2000 |
| WO | WO 01/51041 | 7/2001 |
| WO | WO0149336 * | 7/2001 |
| WO | WO 02/28366 A2 | 4/2002 |
| WO | WO 02/43800 | 6/2002 |
| WO | WO 02/067895 A2 | 9/2002 |
| WO | WO 03/041684 A2 | 5/2003 |
| WO | WO 03/072113 | 9/2003 |
| WO | WO 2004/052336 A2 | 6/2004 |
| WO | WO 2004/089335 A2 | 10/2004 |
| WO | WO 2005/048930 A2 | 6/2005 |

OTHER PUBLICATIONS

Troen et al, "The atherogenic effect of excess methionine intake," PNAS, vol. 100, No. 5, pp. 15089-15094, 2003.*

* cited by examiner

NON-AQUEOUS SINGLE PHASE VEHICLES AND FORMULATIONS UTILIZING SUCH VEHICLES

CROSS-REFERENCE TO RELATED APPLICATION

This application is filed as a continuation-in-part of U.S. Ser. No. 10/814,826, filed Mar. 31, 2004 (published as US 2005/0008661 on Jan. 13, 2005), which claims the benefit of U.S. Ser. No. 60/459,300, filed Mar. 31, 2003, the entire disclosure of which is incorporated herein in its entirety, and further claims the benefit of U.S. Ser. No. 60/650,252, filed Feb. 3, 2005, the entire disclosures of which are incorporated herein in their entirety.

FIELD OF THE INVENTION

This invention relates to vehicles useful in preparing drug formulations. In particular, the invention relates to vehicles that provide an environment that improves the stability of the active component of the drug formulation.

BACKGROUND OF THE INVENTION

A great amount of effort has been devoted to improving methods and materials for delivery of active agents or therapeutics to patients. Oftentimes, the improvements involve increasing the efficiency of drug delivery, improving drug targeting, improving drug delivery profiles, reducing side-effects, or improving drug stability. In some instances, the improvements are achieved by using an excipient, or more particularly a drug delivery vehicle.

Drug delivery vehicles can be employed with implantable devices, some of which are capable of delivering desired doses of a beneficial active agent over extended periods of time. For example, U.S. Pat. Nos. 5,034,229, 5,557,318, 5,110,596, 5,728,396, 5,985,305, 6,113,938, 6,156,331, 6,375,978, and 6,395,292, the contents of each of which are herein incorporated in their entirety by reference, teach osmotically driven devices capable of delivering an active agent formulation, such as a solution or a suspension, at a desired rate over an extended period of time (i.e., a period ranging from more than one week up to one year or more). Other exemplary implantable devices include regulator-type implantable pumps that provide constant flow, adjustable flow, or programmable flow of beneficial agent formulations, which are available from, for example, Codman of Raynham, Mass., Medtronic of Minneapolis, Minn., and Tricumed Medinzintechnik GmbH of Germany. Further examples of implantable devices are described in U.S. Pat. Nos. 6,283,949, 5,976,109, 5,836,935, and 5,511,355, which are herein incorporated in their entirety by reference. This category of implantable devices can be designed to deliver a desired active agent at therapeutic levels over an extended period of time, and, therefore, drug delivery vehicles incorporated with such devices need to account for such extended periods in vivo.

Examples of active agents or drugs contemplated for use with the present invention are biomolecular material that can act as therapeutics. The delivery of such agents over an extended period of time with an implantable drug delivery system has proven difficult for a number of factors. As it is used herein, the term "biomolecular material" refers to peptides, polypeptides, proteins, nucleic acids, viruses, antibodies, and any other naturally derived, synthetically produced, or recombinantly produced active agent that includes nucleic or amino acid. Among other challenges, two problems must be addressed by the device and the delivery vehicle when seeking to deliver biomolecular material over an extended period of time from an implanted delivery device. First, the biomolecular material must be contained within a formulation that substantially maintains the stability of the material at elevated temperatures (i.e., 37° C. and above) over the operational life of the device. Second, the biomolecular material must be formulated in a way that allows delivery of the biomolecular material from an implanted device into a desired environment of operation over an extended period time. This second challenge has proven particularly difficult where the biomolecular material is included in a flowable composition that is delivered from a device over an extended period of time at low flow rates (i.e., $\leq 100$ µl/day).

Biomolecular material may degrade via one or more of several different mechanisms, including deamidation, oxidation, hydrolysis, disulfide interchange, and racemization. Significantly, water is a reactant in many of the relevant degradation pathways. Moreover, water acts as a plasticizer and facilitates the unfolding and irreversible aggregation of biomolecular materials. To work around the stability problems created by aqueous formulations of biomolecular materials, dry powder formulations of biomolecular materials have been created using known particle formation processes, such as by known lyophilization, spray-drying, or dessication techniques. Though dry powder formulations of biomolecular material have been shown to provide suitable stability characteristics, it would be desirable to provide a formulation that is stable over extended periods of time, and, when delivered via an implantable device, is also flowable and readily deliverable from the implantable device.

In the instances when a drug delivery vehicle uses polymeric excipients, such as povidone, crospovidone, and copovidone, these excipients may lead to oxidation of the active agents in the drug formulations due to the presence of peroxides in the polymer preparations. Some examples of active agents that can be sensitive to oxidation, or oxidation-sensitive active agents, include proteins, peptides, ergot alkaloids, and antibiotics such as doxycycline, metformin and molsidomine. Povidone, crospovidone, and copovidone thus have limited utility as solid excipients in formulations containing oxidation-sensitive active agents. To reduce oxidation, freshly prepared polymeric excipients can be used as they typically have lower peroxide levels than polymer excipients that have been stored for a period of time. However, the use of freshly prepared polymer excipients to prepare drug formulations often involves major logistical problems.

Other nonaqueous drug formulations that can be delivered from an implantable device include biomolecular materials that are stable over extended periods of time at elevated temperatures. The nonaqueous vehicle formulations typically include polymers, solvents, and surfactants. Under certain circumstances, when these formulations are exposed to an aqueous liquid, such as a physiological fluid, within a delivery conduit of a device used to deliver the formulations, the polymer included in the vehicle tends to phase separate from the solvent into the aqueous liquid. As the polymer partitions into the aqueous liquid, the concentration of polymer within the aqueous liquid may increase to such an extent that a highly viscous polymer gel or precipitate is formed within the delivery conduit, resulting in a partial or complete occlusion of the delivery conduit and interfering with the desired operation of the delivery device. The potential for such occlusions increases where the geometry of the conduit is such that aqueous liquid interfaces with the drug formulation in a confined area over a relatively long period of time (e.g., hours or days).

A need therefore exists in the art for methods for reducing peroxide levels in delivery vehicles formed from polymer preparations, particularly in drug formulations comprising oxidation-sensitive active agents. There is a further need for such delivery vehicles to be deliverable from an implantable device with reduced potential for occluding a delivery conduit, while providing enhanced stability to the active agent that is intended for delivery.

SUMMARY OF THE INVENTION

An aspect of the present invention provides methods for reducing the level of peroxide in a biocompatible polymer preparation capable of forming a drug delivery vehicle comprising adding methionine to the biocompatible polymer preparation. Some examples of polymers for the biocompatible polymer preparations include polyvinylpyrrolidone, polyethylene glycol, or methyl cellulose. In some embodiments, the methionine is removed from the polymer preparation through a number of steps including diafiltrating, dialyzing, or precipitating.

In another aspect of the present invention, provided are polymer preparations that further comprise solvents and form a stable nonaqueous drug formulation comprising a drug, wherein the drug is insoluble in one or more components of the drug formulation and the drug is stable at 37° C. for at least two months.

In yet other aspects of the present invention, aqueous solutions are provided that have reduced levels of peroxide. The aqueous solutions comprise a polymer preparation and methionine, which is added to the polymer in an amount that yields a weight ratio of methionine to polymer ranging from 1 to 50 to 1 to 2.

In a further aspect of the present invention, stable nonaqueous drug formulations are provided, which have reduced levels of peroxide comprising a polymer; a solvent; methionine in amounts that achieve a weight ratio of methionine to polymer of from 1 to 50 to 1 to 2; and a drug. In this aspect, the drug is insoluble in the polymer or the solvent and the drug formulation is stable at 37° C. for at least two months.

The foregoing general description and the following detailed description are exemplary and explanatory only and are not restrictive of the present invention, which is defined in the appended claims.

BRIEF DESCRIPTION OF THE DRAWINGS

The invention is illustrated by way of example and is not intended to be limited by the accompanying figures.

DETAILED DESCRIPTION OF ILLUSTRATIVE EMBODIMENTS

Figure 1:
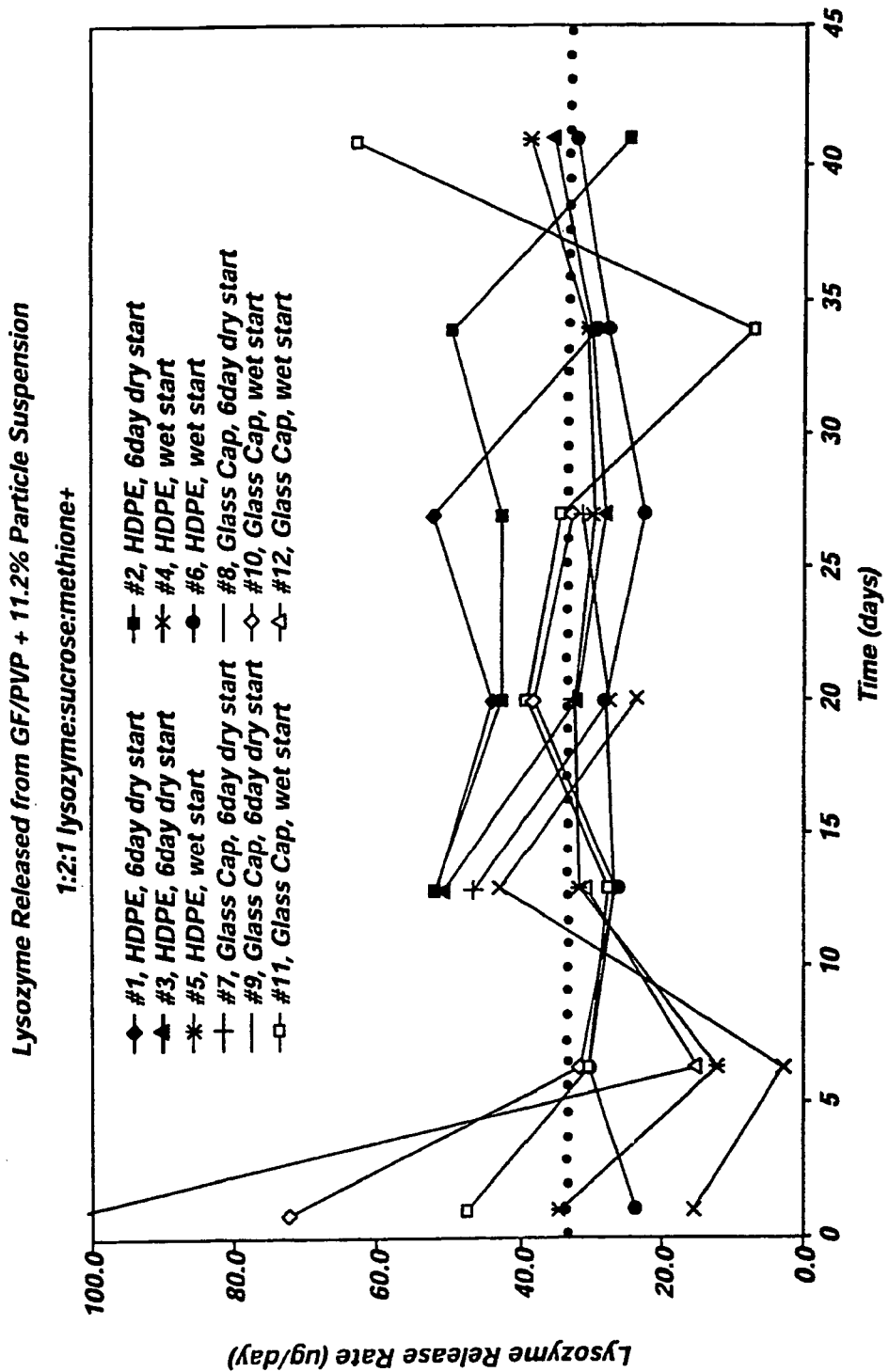
FIG. 1 provides a graph illustrating the release rate performance provided by a lysozyme formulation that was prepared using a vehicle according to an embodiment of the present invention, which was released from osmotic pumps designed to deliver the lysozyme formulation at a rate of 1.5 μl/day over a three-month period of time, providing a targeted lysozyme release rate of 35 μg/day.

Aspects of the present invention include nonaqueous vehicles that are formed using a combination of polymer and solvent that results in a vehicle that is biocompatible and miscible in water. Such vehicles are useful for forming nonaqueous drug formulations. The polymers and solvents used in the drug vehicles according to some aspects of the present invention are chosen to provide a homogeneous system that is substantially uniform, both physically and chemically, throughout, as determined by differential scanning calorimetry (DSC). The drug delivery vehicles are biocompatible, and the polymers and solvents used in the vehicles are chosen and combined such that the resultant vehicle disintegrates or breaks down over a period of time in response to a biological environment. The breakdown of the vehicle in a biological environment may take place by one or more physical or chemical processes, such as by enzymatic action, oxidation, reduction, hydrolysis (e.g., proteolysis), displacement, or dissolution by solubilization, emulsion or micelle formation. After a vehicle of the present invention is broken down in a biological environment, components of the vehicle are then absorbed, or otherwise dissipated, by the body and surrounding tissue.

As used herein, the term "miscible in water" refers to a vehicle that, at a temperature range representative of a chosen operational environment, can be mixed with water at all proportions without resulting in a phase separation of the polymer from the solvent such that a highly viscous polymer phase is formed. As used herein, a "highly viscous polymer phase" refers to a polymer containing composition that exhibits a viscosity that is greater than the viscosity of the vehicle before the vehicle is mixed with water. Because some of the vehicles disclosed do not form a highly viscous polymer phase upon mixture with water, such vehicles allow the creation of drug formulations that work to reduce the occurrence of partial or complete occlusions of the delivery conduits included in delivery devices used to administer the formulations.

Some aspects of the present invention provide methods for reducing the level of peroxide in a polymer preparation capable of forming a drug delivery vehicle comprising adding methionine to the polymer preparation. Preparations of some polymers, e.g., polyvinylpyrrolidone, polyethylene glycol, methylcellulose, and vinylpyrrolidone/vinyl acetate, can contain high levels of peroxide (up to 400 ppm), which tend to increase over time as the preparations are stored. These methods can be used to reduce peroxide levels in preparations of such polymers, including preparations of polymers that are water-soluble. When the polymer preparations are used as excipients in drug formulations or drug delivery vehicles, the peroxide present in the preparations can destabilize biomolecular materials, e.g., oxidation-sensitive active ingredients, which limit the use of such polymeric excipients in formulations containing biomolecular materials. Applicants have surprisingly discovered that treatment of polymer preparations with methionine reduces the level of peroxides in the preparations to a substantially low level, the treatment being over a period of less than 24 hours, preferably about 4 hours. The substantially low level represents a level that allows the polymer preparations to be successfully used as excipients in formulations containing biomolecular materials. Preferably, substantially low levels refer to about a 100 fold reduction in the level of peroxide, and more preferably refer to levels of peroxide at or below 10 ppm, and even more preferably at or below 5 ppm.

Certain aspects of the present invention relate to methods for reducing peroxide levels in preparations of polymers such as, for example, polyvinylpyrrolidone, polyethylene glycol, and methyl cellulose. Preferred embodiments of the invention relate to methods for reducing peroxide levels in preparations of polyvinylpyrrolidone. In certain embodiments of the invention, the methionine and the polymer preparation are mixed following the addition of the methionine to the polymer preparation. Preferably, the polymer preparation and the methionine are mixed for at least ten minutes, and, more preferably, for four to sixteen hours. The polymer preparation and the methionine can, in certain embodiments of the invention, be mixed for up to four days. Any means can be used to mix the methionine and the polymer preparation. In some embodiments of the invention, the weight ratio of methionine to polymer following the addition of the methionine to the polymer preparation is from about 1 to 50 to about 1 to 2. In preferred embodiments, the weight ratio of the methionine to the polymer preparation is from about 1 to 20 to about 1 to 4. In more preferred embodiments, the weight ratio of the methionine to the polymer preparation is from about 1 to 20 to about 3 to 20.

The methionine used to reduce the peroxide levels in polymer preparations according to certain aspects of the invention can be L-methionine or D-methionine, or a combination thereof. Preferably, the methionine is L-methionine if the polymer preparation is intended for administration to humans or animals.

Certain aspects of the invention relate to methods for reducing peroxide levels in preparations of water-soluble polymers that comprise providing an aqueous solution of a preparation of a water-soluble polymer and adding methionine to the aqueous solution. In preferred embodiments of the invention, the aqueous solution of the preparation of the water-soluble polymer comprises from about 0.5% to about 40% by unit weight of the preparation of the water-soluble polymer per unit volume of the aqueous solution. In more preferred embodiments, the aqueous solution of the preparation of the water-soluble polymer comprises from about 1% to about 20% by unit weight of the preparation of the water-soluble polymer per unit volume of the aqueous solution. In still more preferred embodiments, the aqueous solution of the preparation of the water-soluble polymer comprises from about 2% to about 10% by unit weight of the preparation of the water-soluble polymer per unit volume of the aqueous solution.

In certain embodiments, the invention relates to methods for reducing peroxide levels in preparations of water-soluble polymers that comprise providing an aqueous solution of a preparation of a water-soluble polymer, adding methionine to the aqueous solution, and removing the methionine from the aqueous solution of the preparation of the water-soluble polymer. The methionine can be removed using any means, including, for example, diafiltration, dialysis, and precipitation of either the water-soluble polymer of the methionine.

Another aspect of the invention relates to methods for reducing peroxide levels in preparations of water-soluble polymers that further comprise removing water from the aqueous solution of the preparation of the water-soluble polymer following removal of the methionine. In certain embodiments of the invention, substantially all of the water is removed from the aqueous solution of the preparation of the water-soluble polymer. Any means can be used to remove the water from the aqueous solution of the preparation of the water-soluble polymer including, for example, lyophilization, spray drying, drum drying, and fluid bed processing. In embodiments where the polymer is a liquid polymer, water can be removed by one of a number of liquid concentration methods such as diafiltration, extraction, and precipitation.

Aspects of the invention also provide, in certain embodiments, methods for reducing peroxide levels in preparations of water-soluble polymers that comprise providing an aqueous solution of a preparation of a water-soluble polymer, adding methionine to the aqueous solution of the preparation of the water-soluble polymer, removing the methionine from the aqueous solution of the preparation of the water-soluble polymer, removing the liquid from the aqueous solution of the preparation of the water-soluble polymer, and, optionally, adding methionine to the preparation of the dried, methionine-treated water-soluble polymer. Preferably, if the methionine is intended for administration to animals or humans, L-methionine is added to the preparation of the dried, methionine-treated water-soluble polymer.

In another aspect of the present invention, provided are drug formulations that include a drug dispersed within a vehicle according to the present invention. The drug included in a drug formulation according to the present invention is preferably provided as a particulate material. The particulate material may be substantially pure drug material or may be formed of drug particles that include the drug material plus one or more coatings, preservatives, excipients, or adjuvants. Though vehicles according to the present invention are particularly suited for providing drug formulations that incorporate particulate biomolecular material, the formulations of the present invention are not so limited. As it is used herein, the term "drug" refers to any compound or material that provides a therapeutic or beneficial effect and includes biomaterials, such as medicines vitamins, nutrients, and food supplements. However, in each embodiment of a drug formulation of the present invention, the vehicle is chosen and the drug, preferable in the form of a particulate drug material, is prepared such that the drug is not soluble in one or more of the vehicle components.

A vehicle according to the present invention may include any pharmaceutically acceptable polymer that can be combined with a solvent to provide a vehicle that is miscible with water, single-phase, biocompatible, suitable for creating and maintaining drug suspension, and capable of providing a stable drug formulation. Examples of polymers useful in forming a vehicle according to the present invention include, but are not limited to, polyesters such as PLA (polylactic acid) having an inherent viscosity in the range of about 0.5 to 2.0 i.v. and PLOA (polylacticpolyglycolic acid) having an inherent viscosity in the range of about 0.5 to 2.0 i.v., pyrrolidones such as polyvinylpyrrolidone (having a molecular weight range of about 2,000 to 1,000,000), esters or ethers of unsaturated alcohols such as vinyl acetate, polyethylene glycol, methylcellulose, vinylpyrrolidone/vinyl acetate copolymer, and polyoxyethylene/polyoxypropylene block copolymers such as Pluronic 105. If desired, more than one different polymer or grades of single polymer may be used to achieve a vehicle according to the present invention.

Though different polymer and solvent combinations may be used to create a vehicle according to the present invention, the polymer and solvent are chosen and combined in a manner that provides a vehicle that is not only miscible with water, but is also suitable for creating a suspension of drug material that works to maintain the stability of the drug, even when the suspension is exposed to elevated temperatures. As it is used herein, the terms "stable" and "stability" refer to both the chemical and physical stability of a drug material, preferably relating to the duration when the drug is within the drug delivery vehicle. In particular, a drug formulation is considered chemically stable according to the present invention if no more than about 35% of the drug is degraded by chemical pathways, such as by oxidation, deamidation, and hydrolysis, after maintenance of the formulation at 37° C. for a period of two months. Furthermore, a drug formulation is considered physically stable if, under the same conditions, no more than about 15% of the drug substance contained in the formulation is degraded through aggregation. A drug formulation is stable according to the present invention if at least about 65% of the drug remains physically and chemically stable after about two months at 37° C.

In some aspects of the present invention, provided drug formulations are stable when maintained at elevated temperatures, which minimizes the potential for partial or complete occlusion of the delivery passage of a delivery device from which the formulations are delivered, e.g., an implantable device. In preferred embodiments, the drug formulations are formulated such that at least about 80% of the drug included in the formulation remains chemically and physically stable after two months at 40° C. In particularly preferred embodiments, drug formulations are formulated such that more than 90% of the drug included in the formulation remains chemically and physically stable after two months at 40° C., with formulations maintaining the chemical and physical stability of 95% or more of the drug after two months at 40° C. being especially desirable. Moreover, such drug formulations are preferably formulated such that they remain stable when subjected to sterilization by irradiation (e.g., gamma, beta or electron beam) before exposure to elevated temperatures for an extended period of time. Because they are formed using a drug delivery vehicle according to the present invention, certain drug formulations according to an aspect of the present invention are miscible with aqueous liquid that may be present in the delivery conduit of a delivery device used to administer the drug formulations. Such miscibility works to reduce or eliminate the potential for formation of partial or complete occlusion of the delivery conduit, particularly where the drug formulation is delivered at low rates (i.e., $\leq 100$ μl/day) and is in contact with an aqueous liquid within the conduit from which the drug formulation is delivered for a long period of time (i.e., about one day or more).

Aspects of the present invention further includes methods of producing drug formulations, particularly drug vehicles, of the present invention. In one embodiment, methods of producing vehicles according to the present invention include combining the vehicle components and blending such components at elevated temperature until a single-phase material is achieved. Some of the drug formulations according to the present invention are prepared by dispersing a particulate drug material in a vehicle according to the present invention to provide a suspension having a desired distribution of particulate drug material. In one embodiment, a method of preparing a drug formulation according to the present invention includes mixing a particulate drug material with a vehicle according to the present invention at elevated temperatures until a suspension having a desired distribution of particulate drug material is achieved. Methods for producing a vehicle or a drug formulation according to the present invention are preferably carried out without the addition of water to the ingredients used in forming the vehicle, to the vehicle itself, or to the particulate drug material dispersed within the vehicle.

Some of the solvents included in the provided vehicles include solvents that are pharmaceutically acceptable and can be combined with a suitable polymer to provide vehicles that are miscible with an aqueous liquid, single-phase, biocompatible, suitable for creating and maintaining a drug suspension, and capable of providing a stable drug formulation. In some embodiments, the solvent may be water soluble. For instance, benzyl alcohol (BA) is a solvent that may be used to provide a miscible vehicle according to the present invention, even though BA itself is not readily soluble in water. Further examples of solvents that may be used to provide a vehicle according to the present invention include, but are not limited to, glycofurol, tetraglycol, n-methylpyrrolidone, glycerol formal, glycerine, and propylene glycol where desired, two or more solvents may be used to provide a vehicle according to the present invention. In particular, two or more solvents may be required to provide a vehicle that is both miscible in water and facilitates the production of a stable formulation of a chosen drug.

In certain aspects of the present invention, the vehicle may be a Newtonian or a non-Newtonian material, and the viscosity of the vehicle will vary. However, such vehicles are formulated to provide a viscosity that is capable of maintaining a desired suspension of a chosen biomolecular material, such as a particulate drug material, over a predetermined period of time, thereby facilitating creation of a drug formulation tailored to provide controlled drug delivery at a desired rate. Therefore, the viscosity will vary depending on, among other factors, the desired application, the size and type of the particulate drug material to be included in the vehicle, and the required vehicle loading. The viscosity can be varied, as desired, by altering the type or relative amounts of solvent and polymer materials included in the vehicle. In one embodiment, the vehicle is formulated as a viscous vehicle, with the vehicle having a viscosity in the range of about 1,000 to 10,000,000 poise, and preferably from about 10,000 to 250,000 poise. The viscosities mentioned herein are generally measured at 37° C. at a shear rate of $10^{-4}$/sec using a parallel plate rheometer.

Depending on the desired performance characteristics, the amount of polymer and solvent included in a vehicle is varied. Generally, however, vehicles will include about 40% to about 80% (wt/wt) polymer and about 20% to about 60% (wt/wt) solvent. In some instances, preferred embodiments include vehicles formed of polymer and solvent combined at the following ratios: about 25% solvent and about 75% polymer; about 30% solvent and about 70% polymer; about 35% solvent and about 65% polymer; about 40% solvent and about 60% polymer; about 45% solvent and about 55% polymer; and about 50% solvent and about 50% polymer (with all percentages given in wt/wt ratios). However, it is not necessary that the vehicle of the present invention be formed using only polymer and solvent.

Beyond polymers and solvents, a vehicle according to the present invention may also include one or more surfactants or preservatives. Surfactants that may be used in a vehicle according to the present invention include, but are not limited to, esters of polyhydric alcohols such as glycerol monolaurate, ethoxylated castor oil, polysorbates, esters or ethers of saturated alcohols such as myristyl lactate (Ceraphyl 50), and polyoxyethylene/polyoxypropylene block copolymers, such as Pluronic. One or more surfactants maybe included in a vehicle according to the present invention to facilitate release of the drug from the vehicle once a drug formulation according to the present invention is delivered to an environment of operation. Alternatively, one or more surfactants may be included in a vehicle according to the present invention to help maintain the stability of a drug that is to be suspended therein. Where included, a surfactant will typically account for less than about 20% (wt/wt), with preferred ranges of surfactant being less than about 10% (wt/wt), and less than about 5% (wt/wt). Preservatives that may be used in a vehicle according to the present invention include, for example, antioxidants and antimicrobial agents. Examples of potentially useful antioxidants include, but are not limited to, tocopherol (vitamin E), ascorbic acid, ascorbyl palmitate, butylated hydroxyanisole, butylated hydroxytoluene, and propyl gallate. Where one or more preservatives are incorporated in a vehicle according to the present invention, the amount used will vary depending on the application, the preservative used, and the desired result. Generally, a preservative is included only in amounts sufficient to achieve the desired preservative effect.

The particulate drug material included in a drug formulation according to the present invention may be dispersed in a vehicle according the present invention using any mixing, blending, or other dispersion technique that provides a drug formulation having a desired distribution of the particulate drug material. Preferably the particulate drug material is dispersed within the vehicle using a process that does not require the addition of water. For instance, the particulate drug material can be dispersed within a vehicle according to the present invention by combining the vehicle with the particulate drug material under dry conditions and blending the materials under vacuum at an elevated temperature, preferably about 40° C. to about 70° C., until a desired dispersion of the particulate drug material within the vehicle is achieved. The particulate drug material and the vehicle may be blended using the same equipment and techniques used to blend the vehicle. In particular, a mixer, such as a dual helix blade or similar mixer, may be used to blend the particulate drug material and vehicle to achieve a drug formulation according to the present invention. After blending at elevated temperatures, the resulting drug formulation is allowed to cool to room temperature. After preparation, a drug formulation of the present invention may be sealed in a dry container to avoid the undesired incorporation of water.

In some aspects of the present invention, the vehicles are preferably manufactured by combining the desired ingredients without the addition of water. Such vehicles can be prepared by combining the dry (e.g., powdered or low moisture content) ingredients in a dry box or under other dry conditions and blending them at an elevated temperature, preferably about 40° C. to about 70° C., to allow them to liquefy and form a single phase, i.e., a single-phase vehicle. Where a vehicle according to the present invention includes a surfactant, the solvent portion of the vehicle is preferably combined with the surfactant at an elevated temperature before the desired polymer material is added for blending. Blending is preferably completed under vacuum to remove trapped air bubbles produced from the dry ingredients. Once a liquid solution of the vehicle ingredients is achieved, the liquid vehicle may be allowed to cool to room temperature. If desired, the liquid vehicle may be removed from the blending apparatus to allow for cooling. Differential scanning calorimetry may be used to verify that the components included in the vehicle have been combined such that a single-phase materials is formed. The final moisture content of the vehicle is preferably less than 5%.

Some of the vehicles of the present invention facilitate the manufacture of drug formulations that reduce or eliminate the formation of partial or complete occlusions in the delivery channels of devices designed to deliver drug formulations at a controlled rate over an extended period of time, particularly where such devices are implanted or introduced into an environment of operation that includes aqueous liquid. Without being limited to a particular mechanism, it is believed that such performance is due, at least in part, to miscibility of the vehicle with water. Furthermore, it is believed that the miscibility of the vehicle of the present invention with water works to reduce or prevent phase separation of the polymer and solvent materials included in the vehicle when the vehicle comes in contact with an aqueous liquid. As a result, where a drug formulation utilizing a vehicle according to the present invention interfaces with an aqueous liquid in a delivery channel of a delivery device, the polymer included in the vehicle exhibits a reduced tendency to partition into the aqueous liquid in a manner that may result in the partial or complete occlusion of the delivery channel by a polymer precipitate.

A drug formulation according to the present invention includes an amount of a drug that is suspended within a vehicle according to the present invention. Drugs useful in a drug formulation according to the present invention may be provided in the form of pharmaceutically acceptable salts, including salts with inorganic acids, organic acids, inorganic bases, or organic bases. In some embodiments, the drug comprises a particulate material, for example medicines, vitamins, nutrients, or food supplements, which can be a peptide or protein. Preferably, the peptide or protein has a biological activity and may be used to treat a disease or other pathological condition. Specific examples of peptides or proteins that may be used in a drug formulation according to the present invention include, but are not limited to, adrenocorticotropic hormone, angiotensin I and II, atrial natriuretic peptide, bombesin, bradykinin, calcitonin, cerebellin, dynorphin N, alpha and beta endorphin, endothelin, enkephalin, epidermal growth factor, fertirelin, follicular gonadotropin releasing peptide, galanin, glucagon, GLP-1, gonadorelin, gonadotropin, goserelin, growth hormone releasing peptide, histrelin, human growth hormone, insulin, interferons, leuprolide, LHRH, motilin, nafarerlin, neurotensin, oxytocin, relaxin, somatostatin, substances P, tumor necrosis factor, triptorelin, vasopressin, growth hormone, nerve growth factor, blood clotting factors, ribozymes, and antisense oligonucleotides. Analogs, derivatives, antagonists, and agonists of the exemplary peptides and proteins described may also be used. The biomolecular material may also be any compound or material, including any medicine, vitamin, nutrient, or food supplement, which is capable of providing a therapeutic or beneficial affect when administered to an environment of operation and can be prepared as a particulate material exhibiting desired solubility characteristics. To create a suspension of a biomolecular material within a vehicle according to the present invention, the biomolecular material is dispersed within a vehicle according to the present invention as a dry particulate material, meaning that the biomolecular material is present in a solid state (e.g., a powder, crystalline, or amorphous state). When creating a drug formulation according to the present invention, the vehicle is chosen and the particulate biomolecular material is prepared such that the biomolecular material is substantially insoluble in the vehicle. Suitable particulate biomolecular materials, or drugs, and vehicle combinations can be determined by one of skill in the art on the basis of the solubility characteristics. See, for example, Gilman, et. al, The Pharmacological Basis of Therapeutics, $7^{th}$ ed. (1990) and Remington, Pharmacological Sciences, $18^{th}$ ed. (1990), the disclosures of which are incorporated herein by reference.

The amount of particulate drug material included in a drug formulation according to the present invention may vary depending on, among other factors, the potency of the drug, the desired duration of treatment, and the desired release rate of drug. Typically, the particulate drug material accounts for between about 0.1% to 50% (w/w) of a drug formulation according to the present invention, with the vehicle accounting for between about 50% and 99.9% (w/w). In preferred embodiments, a drug formulation according to the present invention includes between about 1% and 30% (w/w) particulate drug material.

Any suitable particle formation process may be used to produce the particulate drug material included in a drug formulation according to the present invention. For example, methods that may be used to create the particulate drug material included in a drug formulation of the present invention include, but are not limited to, known spray drying, lyophilization, dessication, granulation, grinding, milling, precipitation, homogenization, or coating processes. Where the process used to create the particulate drug material does immediately result in a dry product, such as is the case with a wet grinding or wet milling process, the particulate drug matter may be dried by any suitable method until a dried product having a desired moisture content is achieved. The particulate drug material included in a drug formulation according to the present invention may consist of substantially pure drug or it may include particles that include the drug and one or more other substances, such as bulking agents, stabilizers, preservatives, coating materials or other adjuvants or excipients that provide a desired particulate drug material. Though in may not be desired or necessary with all such substances, preparing certain drug substances as particulate materials that include one or more stabilizers, bulking agents, or preservatives can reduce the formation of degradation products (e.g., unstable chemical intermediates). Stabilizers, bulking agents, preservatives, and coating materials, as well as adjuvants or excipients, that may be useful in the formation of a particulate drug material that can be included in a drug formulation according to the present invention are well known in the art. The type and amounts of each such agent will vary depending on, among other factors, the drug to be delivered and the stability and solubility characteristic desired of the particulate drug material.

The vehicle and drug formulation according to the present invention may be loaded into, and delivered from, any device capable of delivering a vehicle or drug formulation according to the present invention at a predetermined rate over a desired period of time. For example, vehicles and drug formulations according to the present invention may be delivered from osmotically driven pumps, such as those taught in U.S. Pat. Nos. 3,797,492, 3,987,790, 4,008,719, 4,865,845, 5,057,318, 5,059,423, 5,112,614, 5,137,727, 5,151,093, 5,234,692, 5,234,693, 5,279,608, 5,336,057, 5,728,396, 5,985,305, 5,997,527, 5,997,902, 6,113,938, 6,132,420, 6,217,906, 6,261,584, 6,270,787, and 6,375,978, the contents of which are herein incorporated in their entirety by reference. However, the vehicle and drug formulation of the present invention are not limited in application to osmotically driven pumps. For instance, the vehicle and drug formulation according to the present invention may also be delivered using pumps driven by chemical or electromechanical means. Examples of such pumps are well known in the art. Moreover, even though the vehicle and drug formulation of the present invention are suited to delivery from an implanted device, the vehicle and drug formulation may also be delivered from a device that is not implantable or implanted. Additionally, the vehicle or drug formulation can be used without a device as a drug depot.

As used herein, the term "delivery vehicle" refers to a molecule or composition useful for holding or suspending and transporting a drug in vivo for ultimate release or delivery. "Delivery vehicle" is used interchangeably with terms such as a "vehicle" or "drug delivery vehicle". The vehicle is formed from one or more pharmaceutical excipients known in the art which provides a stable environment for a drug and facilitates its delivery, preferably a polymeric material. More particularly, the terms "single-phase vehicle" or "single-phase drug delivery vehicle" refer to a delivery vehicle that is substantially a homogeneous system i.e., uniform, both physically and chemically, throughout, as determined by, inter alia, differential scanning calorimetry (DSC). The drug delivery vehicle combined with the drug forms a "drug formulation," which can optionally include other drug excipients.

As used herein, the terms "polymer", "polymeric substance" or "polymeric material" refers to a pharmaceutical excipient that consists of repeating monomer units, including homopolymers that contain a single type of monomer unit and copolymers that contain two or more types of monomer units, that are biocompatible and can form a delivery vehicle for carrying a desired drug for eventual delivery. Preferred examples of a polymer are polyvinylpyrrolidone, polyethylene glycol, or methyl cellulose.

As used herein, the terms "polymer preparation," "preparation of a polymer," and all variations thereof, refer to a preparation of a polymer (or combination of polymers) as contemplated by the present invention, and are used to prepare drug delivery vehicles. The polymer preparations can be selected so that they form drug delivery vehicles with desired properties that enable the transport of a desired drug and delivery of such drug to a desired site in vivo.

As used herein, the term "biomolecular material" refers to an active agent that includes peptides, polypeptides, proteins, nucleic acids, viruses, antibodies, and molecules that mimic the same, among others. The term "drug" is a subset of "biomolecular material"; however, in general, drug can be used interchangeably for biomolecular material when the biomolecular material is one used for therapeutics, and especially when the drug is susceptible to oxidative degradation. The biomolecular materials of the invention are intended to be carried within a delivery vehicle that provides a stable environment and transports the biomolecular material for delivery in vivo, and sometimes, more specifically, to a desired physiological site. Generally, biomolecular materials are susceptible to oxidation over time, and, in particular, certain biomolecular materials, which have been denoted herein as "oxidation-sensitive active agents", have increased sensitivity to oxidation, i.e., concerns over activity loss due to oxidation, such as proteins, e.g., omega-interferon (omega-IFN), peptides, ergot alkaloids, and antibiotics such as doxycycline, metformin and molsidomine, for example.

As used herein, the terms "reduce," "reducing," and all variations thereof, refer to decreasing by any measurable degree the level of peroxide present in a polymer preparation.

As used herein, the term "water-soluble" refers to a substance that is capable of being dissolved in water to some measurable extent.

As used herein, the term "aqueous solution" refers to a solution that contains at least some measurable amount of water.

As used herein, the terms "mixing," "mix," "adding," and "add," and all variations thereof, refer to any means that directly or indirectly cause placement together of moieties or components, such that the moieties or components come into close proximity to each other. The terms include acts such as placing the moieties or components together in a container, combining the moieties or components, contacting the moieties or components, or stirring, vortexing, or agitating the moieties or components together. The term "mixture" refers to moieties or components that have been placed together in close proximity.

As used herein, the terms "removing," "remove," and all variations thereof, refer to the reduction by any measurable degree of the level of methionine present in a polymer preparation. The term "removing substantially all," and all variations thereof, refers to the reduction by at least 50% of the level of methionine present in a polymer preparation.

Unless otherwise defined, all technical and scientific terms used herein have the same meaning as commonly understood by one of ordinary skill in the art to which this invention belongs. In case of conflict, the present specification, including definitions, will control.

EXAMPLES

The following examples are illustrative of a sample of embodiments of the present invention and should not be considered to limit the scope of the invention.

Example 1

Three different exemplary vehicles according to the present invention were produced using Glycofurol ("GF") and polyvinylpyrrolidone ("PVP"). The PVP included in each of the three vehicles was obtained from BASF (17 pf) and had a molecular weight below 18,000 MW. The first vehicle included 42% (wt/wt) GF and 58% (wt/wt) PVP. The second vehicle included 40% (wt/wt) GF and 60% (wt/wt) PVP, and the third vehicle included 50% (wt/wt) GF and 50% (wt/wt) PVP. In each instance, the vehicles were created by first charging the raw materials into a mixer. The raw materials were then blended at about 60° C. under vacuum (about −27 in Hg) for two hours to achieve a single-phase vehicle. Each of the three vehicles was miscible with water in all proportions.

Example 2

A lysozyme formulation according to the present invention was manufactured using the second vehicle of Example 1 and dry, particulate lysozyme material. The lysozyme particles used in the formulation included 1 part lysozyme to two parts sucrose, and 1 part methionine, and the particles were spray dried from a solution including a 25 mM citrate buffer. The simulated drug formulation included 11.2% (wt/wt) lysozyme. The lysozyme formulation was prepared by loading appropriate amounts of the vehicle and the lysozyme particles into a mixer. The particles and vehicle were then blended at about 60° C. under vacuum (about −27 in Hg) until a formulation having a substantially uniform suspension of lysozyme particles was achieved.

Example 3

The deliverability of the lysozyme formulation of Example 2 was evaluated using two groups of six osmotic pumps. The osmotic pumps were designed to deliver the lysozyme formulation at 1.5 μl/day over a three-month period of time, providing a targeted lysozyme release rate of 35 μg/day. To evaluate the release rate performance provided by the lysozyme formulation, the osmotic pumps were introduced into an aqueous media that included a phosphate buffer system (PBS) and was maintained at 37° C.

The first group of 6 osmotic pumps was prepared using the following components:

Reservoir: Titanium alloy
Piston: C-flex
Lubricant: silicone medical fluid
Osmotic Composition: two osmotic tablets (40 mg osmotic engine tablets formed using 76.4% NaCl, 15.5% sodium carboxymethyl cellulose, 6% povidone, 0.5% Mg Stearate, and 1.6% water)+PEG 400 filler
Semipermeable Membrane: polyurethane polymer, injection molded to desired plug shape
Diffusion Moderator: high density polyethylene (HDPE) configured to provide a 10 mil spiral delivery conduit having a 0.25 mm diameter.
Simulated Drug formulation: 11.2% lysozyme particles (lyso:sucro:meth (1:2:1 and 25 mM citrate) in a vehicle of 60% PVP and 40% GF To prepare the first group of osmotic pumps, the piston and the inner diameter of the reservoir were first lightly lubricated using the silicon medical fluid. The piston was then inserted 0.5 cm into the reservoir at the membrane end of the reservoir. An amount of PEG 400 was then introduced into the membrane end of the reservoir and the two osmotic tablets were inserted into the same end to complete the osmotic composition. After insertion of the osmotic engine tablets, the resulting osmotic composition was flush with the membrane end of the reservoir. A semipermeable membrane plug (hereinafter "the membrane plug" or "plug") was inserted into the reservoir by lining up the plug with the membrane end of the reservoir and pushing gently until the retaining features of the plug were fully engaged in the reservoir. The lysozyme formulation was loaded into a syringe, which was then used to fill the reservoir from the outlet end (opposite the membrane end) by injecting the lysozyme formulation into the reservoir until the formulation was about 3 mm from the end. The filled reservoir was centrifuged (outlet end "up") to remove any air bubbles that trapped in the lysozyme formulation during filling. The diffusion moderator was screwed into the outlet end of the reservoir until completely engaged. As the diffusion moderator was screwed in, excess amount of lysozyme formulation exited out of the delivery conduit, ensuring a uniform fill.

The second group of six osmotic pumps was manufactured using the same components and methods as were used to manufacture the first group of osmotic pumps, except that the second group of osmotic pumps utilized diffusion moderators. Instead of a diffusion moderator formed of an HDPE plug that creates a spiral-shaped delivery, the diffusion moderator included in the second group of osmotic pumps was formed of a 0.3 mm square glass capillary glued into an HDPE plug. The glass capillary formed a generally straight delivery conduit.

The release rate performance exhibited by each of the osmotic pumps, including both the first group and the second group, is illustrated in FIG. 1. As indicated in the figure, three osmotic pumps from each group were "wet started" and three osmotic pumps from each group were "dry started." As they are used herein, the term "wet start" or "wet started" indicates that the osmotic pumps were primed such that the osmotic pumps were pumping before introduction into the PBS media for release rate testing, and the term "dry start" or "dry started" indicates that the osmotic pumps were not primed before introduction into the PBS media for release rate testing. Priming of the wet started osmotic pumps was carried out simply by positioning the membrane included in the osmotic pumps in PBS media until the osmotic pumps were pumping at a desired rate. After 40 days of operation in the PBS media, each of the twelve osmotic pumps was still functioning and, in general, delivering amounts of lysozyme that were at or near the targeted delivery rate.

Example 4

Additional vehicles according to the present invention were prepared and their miscibility characteristics were evaluated. Four different vehicles including benzyl alcohol ("BA") as a solvent and PVP as a polymer were prepared. Two different grades of PVP (12 pf and 17 pf) from BASF were used in the preparation of these vehicles. The first vehicle included 40% (wt/wt) BA and 60% (wt/wt) PVP 17 pf. The second vehicle included 38% (wt/wt) BA and 62%. (wt/wt) PVP 17 pf. The third vehicle included 26% (wt/wt) BA, 37% (wt/wt) PVP 12 pf, and 37% (wt/wt) PVP 17 pf, and the fourth vehicle included 27% (wt/wt) BA, 36.5% (wt/wt) PVP 12 pf and 36.5% (wt/wt) PVP 17 pf. In each instance, the vehicles were created by first charging the raw materials into a mixer. The raw materials were then blended at 50° C. under vacuum (about −28 in Hg) for 60 to 90 minutes, resulting in single-phase vehicles according to the present invention.

Each of the four BA/PVP vehicles prepared according to this Example exhibited desirable miscibility characteristics. To evaluate the miscibility characteristics of these vehicles, water or a phosphate buffer solution was added to each vehicle in varying amounts to determine when, or if any, phase separation could be observed. With each of the four vehicles prepared, no phase separation was observed until the water or phosphate buffer content increased to 50% or more, at which point the PVP included in the vehicle was too dilute to precipitate or form a highly viscous polymer material.

Example 5

Yet another exemplary vehicle was prepared according to the method described in Example 4, except that the vehicle was formulated using 36% (wt/wt) BA, 32% (wt/wt) PVP 12 pf, and 32% (wt/wt) PVP 17 pf. The miscibility characteristics of lysozyme formulations prepared using this vehicle were then evaluated.

Four different lysozyme formulations were prepared. Each of the formulations was prepared using the vehicle prepared in this example as well as one of four different particulate lysozyme compositions. The particulate lysozyme compositions were prepared by spray-drying lysozyme formulations prepared using a citrate buffer. The particles of the first particulate lysozyme composition included 1 part lysozyme to 2 parts sucrose. The particles of the second particulate composition included 1 part lysozyme to 2 parts sucrose and 1 part methionine. The particles of the third particulate lysozyme composition included 1 part lysozyme to 3 parts sucrose and 1 part dextran, and the particles of the fourth particulate lysozyme composition included 1 part lysozyme to 3 parts sucrose, 1 part methionine, and 1 part dextran. To prepare each of the four lysozyme formulations, a vehicle prepared according to this example was combined with each of the four particulate lysozyme compositions such that, in each case, a substantially uniform suspension having 10% particle loading was achieved. Blending of the particulate lysozyme compositions and the vehicle was carried out at 60° C. under vacuum (about −28 in Hg).

Once each of the four lysozyme formulations was prepared, a phosphate buffer solution was added to each and the phase behavior of the four formulations was observed. As was true of the vehicles prepared in Example 4, the four lysozyme formulations exhibited desirable miscibility characteristics. With each of the four lysozyme formulations, no phase separation was observed until the phosphate buffer content increased to 50% or more, at which point the PVP included in the vehicle was too dilute to precipitate or form a highly viscous polymer material.

Example 6

The stability of an exemplary drug incorporated in drug formulations according to the present invention was evaluated. To evaluate the stability of a drug formulation according to the present invention, two different drug formulations were prepared and stored in titanium reservoirs over a period of three months at a temperature of 5° C., 25° C., or 40° C. After storage of the drug formulations over the three-month period, the stability of the drug included in each formulation was evaluated using reverse phase, high performance liquid chromatography (RP-HPLC) and size exclusion chromatography (SEC).

The drug used in both drug formulations of this example was omega-interferon. The omega-interferon was prepared as a particulate composition, which included particles formulated to include 1 part omega-interferon to 2 parts sucrose and 1 part L-methionine. The omega-interferon particles were spray dried from a formulation including 25 mM citrate buffer, and as a result, the omega-interferon particles formed also included 7 parts citrate for every 4 parts omega-interferon. In preparing the formulation to be spray dried, a 2% solids content was targeted. When spray drying the omega-interferon particles, a pump rate of 4 ml/min was used. The inlet temperature was 120° C., and the outlet temperature was 85° C.

The vehicle used in both drug formulations included 40% BA and 60% PVP 17 pf. Before blending, however, both the BA and PVP materials were processed to remove peroxides to a level of less than 5 ppm. To remove peroxides from the BA material, alumina was mixed with the BA for 30 minutes, after which the BA was filtered through a 0.2µ filter and stored in a sealed vial under nitrogen. To remove peroxides from the PVP material, the PVP was treated with 1% L-methionine solution, diafiltered using a Millipore TTF system to remove residual L-methionine, and lyophilized. Peroxide levels in the processed BA and PVP materials were measured using an OXIS test kit, and moisture levels in the processed materials were measured using Karl Fisher titration. Both the BA and the PVP were processed to achieve moisture levels below 3% and peroxide values below 5 ppm. After suitable moisture content and peroxide levels were achieved, suitable amounts of the processed BA and PVP were charged into a mixer and blended at 50° C. under vacuum (−28 in Hg), until a single-phase vehicle was formed (typically, 60 to 90 minutes). After blending, the moisture content and the peroxide level of the vehicle was confirmed to be less than 3% and less than 5 ppm, respectively.

Both the first and the second formulations were formed using the vehicle and omega-interferon particles described in this Example. However, the two drug formulations were prepared with different amounts of particulate omega-interferon. The first drug formulation (Formulation A) was prepared with a particle loading of 9.6% (wt/wt) and the second drug formulation (Formulation B) was prepared with a particle loading of 3.8% (wt/wt), with the vehicle accounting for the remainder of the formulation in each instance. To prepare the drug formulations, appropriate amounts of the omega-interferon particles and the vehicle were loaded into a mixer and mixed at 60° C. under vacuum (−28 in Hg), until a substantially uniform suspension of the omega-interferon particles was achieved in the vehicle. After mixing, the resulting drug formulations were placed in an oven at 50° C. and subjected to a vacuum to remove residual air bubbles that may have been blended into the drug formulations as a result of the mixing.

To evaluate the stability of the drug formulations prepared, the formulations were loaded into titanium reservoirs that were lubricated with silicon medical fluid and sealed with fluoroelastomer pistons. Formulation A and Formulation B were loaded into titanium reservoirs that were stored for 3 months at 5° C., 25° C., and 40° C. After storage of the exemplary drug formulations in the titanium reservoirs at the designated temperature conditions, the degradation of omega-interferon by oxidation and deamidation was evaluated using HPLC, and the degradation of omega-interferon by aggregation was evaluated using SEC. The results of the study are illustrated in FIG. 2, FIG. 3, and FIG. 4.

Figure 2:
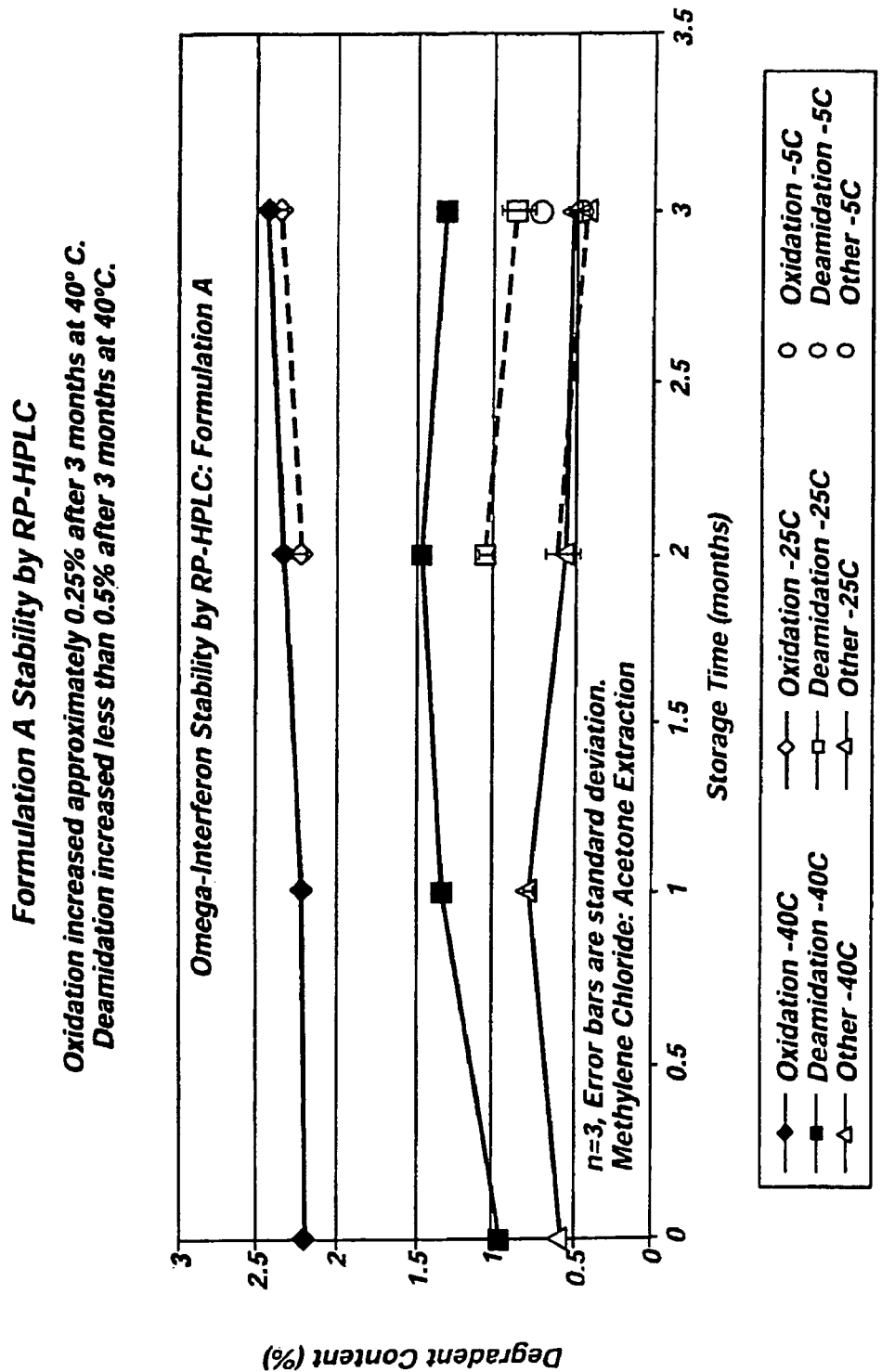
FIG. 2 illustrates the increase in oxidation and deamidation of omega-interferon included in a first exemplary drug formulation prepared according to the present invention (Formulation A), after such formulation was stored at 5° C., 25° C., and 40° C. for three months.

FIG. 2 illustrates the increase in oxidation and deamidation of the omega-interferon that occurred in Formulation A during storage of the formulation in the titanium reservoirs at the designated temperatures. As can be appreciated by reference to FIG. 2, Formulation A provided desirable stability characteristics. In particular, even after storage of Formulation A at 40° C. for three months, oxidation of the drug increased approximately 0.25% and deamidation of the drug increased less than 0.5%.

Figure 3:
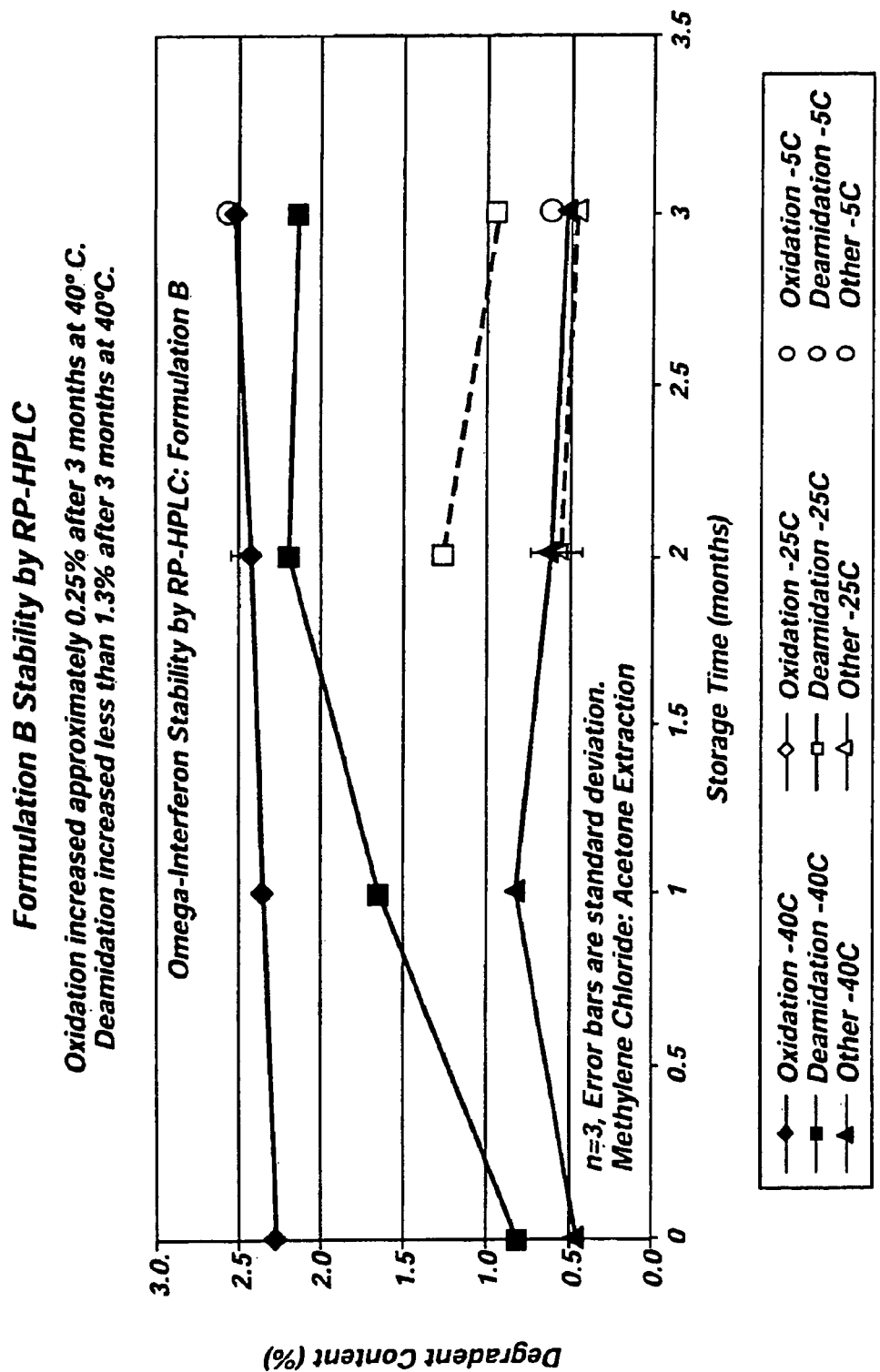
FIG. 3 illustrates the increase in oxidation and deamidation of omega-interferon included in a second exemplary drug formulation prepared according to the present invention (Formulation B), after such formulation was stored at 50° C., 25° C., and 40° C. for three months.

FIG. 3 illustrates the increase in oxidation and deamidation of the omega-interferon that occurred in Formulation B during storage of the formulation in the titanium reservoirs at the designated temperatures. As can be appreciated by reference to FIG. 3, Formulation B also provided desirable stability characteristics. Even after storage of Formulation B at 40° C. for three months, oxidation of the drug increased approximately 0.25% and deamidation of the drug increased approximately 1.3%.

Figure 4:
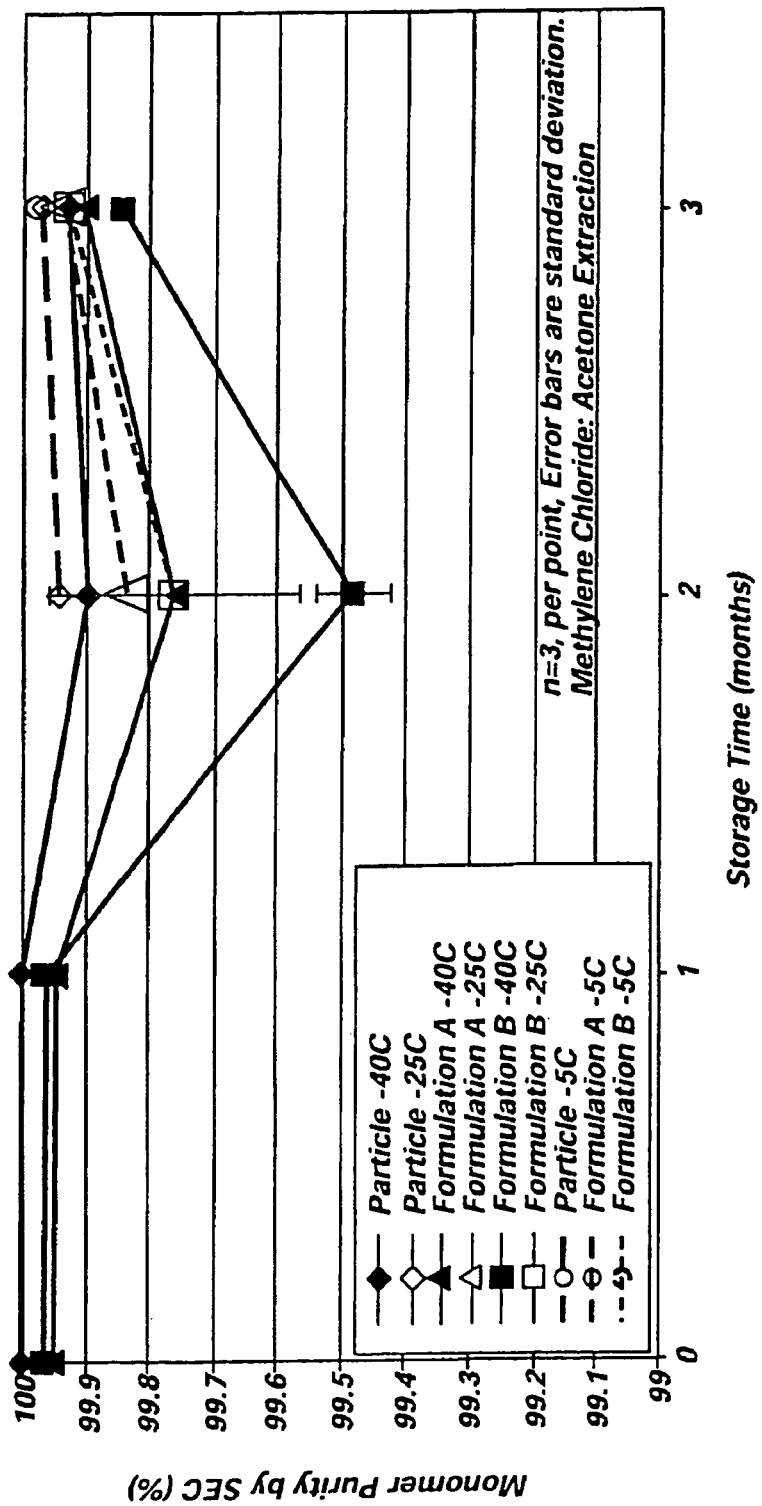
FIG. 4 illustrates the omega-interferon monomer stability provided by Formulation A and Formulation B after such formulations were stored at 5° C., 25° C., and 40° C. for three months.

FIG. 4 illustrates the amount of aggregates formed in both Formulation A and Formulation B when stored in titanium reservoirs at the designated temperatures over the three-month period of time. As can be appreciated by reference to FIG. 4, Formulation A and Formulation B again exhibited desirable stability characteristics, with no significant amounts of drug aggregation occurring in either formulation, even after storage for three months at 40° C.

Example 7

Quantitative Assay for Peroxide Detection in Polyvinylpyrrolidone Preparations

A BIOXYTECH® $H_2O_2$-560™ assay and reagent kit (OXIS International Inc.), which involves the calorimetric quantitative determination of $H_2O_2$ (total hydroperoxides) in test samples, was used to determine the peroxide level in polyvinylpyrrolidone preparations.

The assay is based on the oxidation of ferrous ions ($Fe^{2+}$) to Ferric ions ($Fe^{3+}$) by hydrogen peroxide under acidic conditions. The ferric ion binds the indicator xylenol orange to form a stable colored complex that can be measured at 560 nm:

$$Fe^{2+} + H_2O_2 \rightarrow Fe^{3+} + HO \cdot + OH^- \quad (1)$$

$$Fe^{3+} + XO \rightarrow Fe^{3+} - XO \quad (2)$$

Fresh standards were prepared for each experiment according to the following procedure. A 25 mM $H_2O_2$ stock solution was prepared by diluting 142.5 µL of 30% $H_2O_2$ to 50 mL with Milli-Q water. The stock solution was standardized using 43.6 $M^{-1}$ $cm^{-1}$ as the total molar extinction coefficient for $H_2O_2$ at 240 nm and the actual concentration in mM was calculated.

A standard 100 µM $H_2O_2$ solution was prepared by mixing 100 µL of the standardized 25 mM $H_2O_2$ stock solution with 25 mL milli-Q water. Both components of the solution (the 100 µM $H_2O_2$ stock solution and the milli-Q water) were weighed and the actual concentration of the resulting solution was calculated based on a density of 1 g/mL for each component.

A range of additional $H_2O_2$ standard solutions was prepared according to Table 1 below. Both components of the solutions (the 100 µM $H_2O_2$ stock solution and the milli-Q water) were weighed and the actual concentrations of the resulting solutions were calculated based on a density of 1 g/mL for each component.

TABLE 1

Peroxide standard solutions

| | | 100 μM stock sol'n | | | | | Actual |
|---|---|---|---|---|---|---|---|
| | Target | | | Actual | $H_2O$ | | Standard |
| Standard sol'n ID | conc., μm | Theoret., mg | Actual, mg | conc., μM | Theoret., mg | Actual, mg | conc., μM |
| S01 | 0.5 | 50 | | | 9950 | | |
| S02 | 1 | 100 | | | 9900 | | |
| S03 | 2 | 200 | | | 9800 | | |
| S04 | 5 | 50 | | | 950 | | |
| S05 | 10 | 100 | | | 900 | | |
| S06 | 12 | 120 | | | 880 | | |
| S07 | 15 | 150 | | | 850 | | |
| S08 | 50 | 500 | | | 500 | | |

The following polyvinylpyrrolidone sample solutions were prepared: a 40 mg/mL solution of untreated polyvinylpyrrolidone, or polyvinylpyrrolidone treated for peroxides that had a $H_2O_2$ level between 40 ppm and 300 ppm; a 10 mg/mL solution of untreated polyvinylpyrrolidone that had a $H_2O_2$ level higher than 300 ppm; and a 100 mg/mL solution of polyvinylpyrrolidone that had been treated for peroxides.

Dilutions of the polyvinylpyrrolidone sample solutions were prepared using the dilution factors shown in Tables 2 and 3.

TABLE 2

Dilution factors for untreated polyvinylpyrrolidone

| Sample # | PVP stock solution μL | Milli-Q $H_2O$, μL | Dilution factor |
|---|---|---|---|
| 1 | 100 | 900 | 10 |
| 2 | 100 | 1900 | 20 |
| 3 | 20 | 980 | 50 |
| 4 | 200/(20 dilut.) | 800 | 100 |
| 5 | 100/(20 dilut.) | 900 | 200 |

TABLE 3

Dilution factors for treated polyvinylpyrrolidone

| Sample # | PVP stock solution μL | Milli-Q H2O, μL | Dilution factor |
|---|---|---|---|
| 1 | 300 | 0 | 1 |
| 2 | 200 | 200 | 2 |
| 3 | 250 | 750 | 4 |
| 4 | 50 | 950 | 20 |

The reagent mix consisted of a mixture of solution R1 (25 mM ammonium iron (II) sulfate, 2.5 M $H_2SO_4$) and solution R2 (100 mM sorbitol, 125 μM xylenol orange in water) in ratio R1:R2=1:100.

The SoftMax software version 3.13 template was set up according to the layout of the wells in the 96 well micro-plates used for the assay. The standard curve was set to linear fit.

200 μL of Milli-Q water was dispensed in each well of a micro-plate and the plate was read to establish a background for the elimination of interference from the plate material.

70 μL of each polyvinylpyrrolidone sample, each standard solution, and a blank water sample were mixed with 700 μL of the prepared reagent mix and the mixture was incubated for at least 30 minutes at room temperature. A multi-channel pipette was used to dispense three 200 μL aliquots of each solution into the wells of a micro-plate and the plate was scanned at a wavelength of 560 nm with a SpectraMax Plus micro-plate reader.

SoftMax software Version 3.13 was used to calculate the concentration of $H_2O_2$ in each sample.

Example 8

Removal of Peroxides from Polyvinylpyrrolidone Preparations

The experiments described below were preformed to evaluate and compare the efficacy of various means for removing peroxides from polyvinylpyrrolidone preparations. The peroxide removal means evaluated were the use of methionine, the use of palladium as a peroxide removal catalyst, the use of alumina ($Al_2O_3$) as a sorbent for the removal of peroxides, and the use of ammonia ($NH_4OH$) as a pH modifier for the removal of peroxides.

The Use of Methionine for the Removal of Peroxides

Optimization of the Amount of Methionine Used for the Removal of Peroxides

The following experiments were performed to optimize the amount of methionine used for the removal of peroxides from polyvinylpyrrolidone preparations. Five 10% aqueous solutions (w/v) of polyvinylpyrrolidone were prepared and DL-methionine was added to the solutions in accordance with Table 4.

TABLE 4

Optimization of the amount of methionine needed to effectively remove peroxides from polyvinylpyrrolidone

| | % PVP solution (w/v) | | | | |
|---|---|---|---|---|---|
| | 10 | 10 | 10 | 10 | 10 |
| % methionine used (w/w methionine/PVP) | 1 | 5 | 10 | 20 | 22 |

Following the addition of methionine, the solutions were mixed for 4 hours at room temperature, filtered through a 0.2 μm filter, and diafiltered through a 1 kD diafiltration membrane to remove the DL-Methionine from the polyvinylpyrrolidone solution. Milli-Q water was used as the diafiltration media and the diafiltration process was continued until the volume of the water that had passed through the solution reached 13 times the volume of the initial polyvinylpyrrolidone solution. The solution was then concentrated to about 60% of the initial solution volume, filtered through a 0.2 μm Nalgene filter, dispensed into 10 mL lyophilizing vials, and lyophilized. The lyophilizing process parameters are shown in Table 5.

TABLE 5

Lyophilizing process parameters

| | | Shelf conditions | | Condenser conditions | | |
|---|---|---|---|---|---|---|
| Time min | Ramping ° C./min | Target temperature ° C. | Pressure relative to absolute vacuum* mT | Target temperature ° C. | Foreline pressure* mT | Note |
| 30 | −2.5 | −50 | N/A | N/A | N/A | Freezing |
| 300 | N/A | −50 | N/A | N/A | N/A | Holding |
| N/A | N/A | −50 | N/A | −40 | N/A | Switching on the condenser |
| N/A | N/A | −50 | ≦150 | ≦−40 | ≦100 | Starting the vacuum pump |
| ≧5100 | +0.16 | 40 | ≦200 | ≦−40 | ≦100 | Drying |

*The pressure was created by a vacuum pump and the numbers in the table represent absolute pressure relative to the absolute zero.

The level of peroxides present in the polyvinylpyrrolidone preparations was determined using the procedures described in Example 1.

Figure 5:
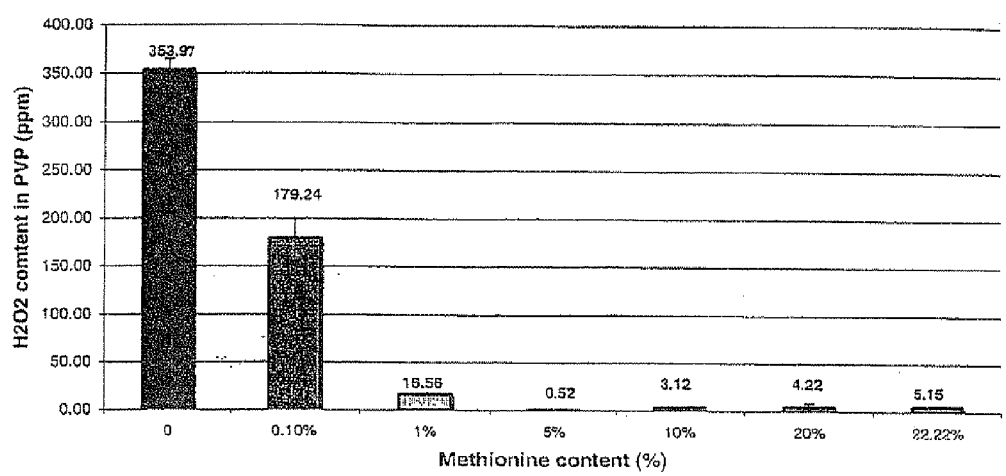
FIG. 5 depicts the results of experiments in which the amount of methionine used for the removal of peroxide from polyvinylpyrrolidone was optimized.

As shown in Table 6 and FIG. 5, when 5% to 10% methionine (w/w methionine/polyvinylpyrrolidone) was added to a 10% (w/v) aqueous solution of polyvinylpyrrolidone, the peroxide content of the polyvinylpyrrolidone was reduced from ~350 ppm to less than 5 ppm.

TABLE 6

Results of optimization of the amount of methionine needed to effectively remove peroxides from polyvinylpyrrolidone

| | Methionine amount, % | | | | | |
|---|---|---|---|---|---|---|
| | 0 | 0.10% | 1% | 5% | 10% | 20% | 22.22% |
| $H_2O_2$ (ppm) | 353.97 | 179.24 | 16.56 | 0.52 | 3.12 | 4.22 | 5.15 |
| StdDev | 11.059 | 20.432 | 0.714 | 0.114 | 0.002 | 4.495 | 0.047 |

Optimization of the Diafiltration Process

The following experiments were performed to determine the amount of water relative to the initial polyvinylpyrrolidone solution volume that was required to effectively remove the methionine from the polyvinylpyrrolidone solution. Twenty grams of polyvinylpyrrolidone were dissolved in Milli-Q water to obtain 200 mL of a polyvinylpyrrolidone solution. Two grams of DL-methionine were then added to the polyvinylpyrrolidone solution, and the solution was mixed at room temperature for 4 hours. An AMICON diafiltration cell was used for diafiltration. The polyvinylpyrrolidone/methionine solution was filtered through a 0.2 μm filter, and poured into the diafiltration cell. The feed liquid reservoir was initially filled with volume 1 ($V_1$, see Table 7) of Milli-Q water and the system was pressurized with nitrogen through the pressure supply line. The system was stopped after all the water was depleted from the reservoir, and a 5-mL sample was taken from the solution and placed in a refrigerator. The amount of water that had passed through the cell was recorded. The procedure was repeated eight times, and the amount of water that had been used for diafiltration during each experiment was recorded, as shown in Table 7.

TABLE 7

Optimization of diafiltration

| | Water Volume ID | | | | | | | | |
|---|---|---|---|---|---|---|---|---|---|
| | $V_1$ | $V_2$ | $V_3$ | $V_4$ | $V_5$ | $V_6$ | $V_7$ | $V_8$ | $V_9$ |
| Water volume, through the cell, mL | 500 | 500 | 500 | 250 | 250 | 200 | 200 | 100 | 100 |
| Total water volume, mL | 500 | 1000 | 1500 | 1750 | 2000 | 2200 | 2400 | 2500 | 2600 |
| $V_w/V_{sol}$ | 2.5 | 5 | 7.5 | 8.75 | 10 | 11 | 12 | 12.5 | 13 |

$V_w$ = Diafiltration water volume through the cell;
$V_{sol}$ = Initial polyvinylpyrrolidone solution volume The samples were lyophilized using the lyophilizing process parameters shown in Table 5, and were then tested for residual methionine.

As show shown in Table 8, when the $V_w/V_{sol}$ ratio was between 8.75 and 10, no methionine was detected in the dry polyvinylpyrrolidone.

TABLE 8

Results of optimization of diafiltration

| | Methionine content, % (w/w methionine/PVP) | | |
|---|---|---|---|
| $V_w/V_{sol}$ | $1^{st}$ 200 ml lot | $2^{nd}$ 200 ml lot | 400 ml lot |
| 0 | 8.7 | 7.962 | 11.225 |
| 2.5 | 0.47 | 0.911 | N/A |
| 5 | 0.07 | 0.062 | N/A |
| 7.5 | 0.003 | 0.008 | N/A |
| 8 | N/A | N/A | 0.010 |
| 8.75 | 0 | 0.000 | N/A |
| 10 | 0 | 0.000 | 0.000 |
| 11 | 0 | 0.000 | N/A |
| 12 | 0 | 0.000 | N/A |
| 12.5 | 0 | 0.000 | N/A |
| 13 | 0.002 | 0.000 | N/A |

The Use of Palladium for the Removal of Peroxides

Figure 6:
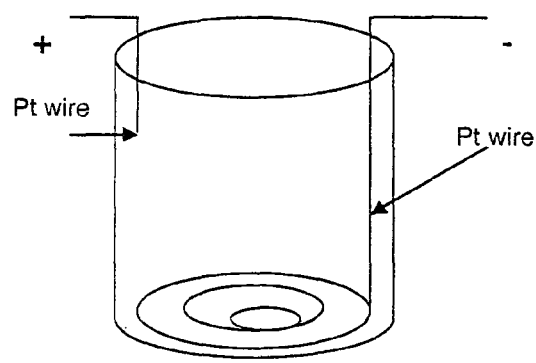
FIG. 6 depicts an electrolyte cell used for the hydrogenation of palladium.

Twelve volts of direct current were used to hydrogenate palladium granules over the course of two days using the electrolyte cell shown in FIG. 6. Eight grams of palladium granules were spread over the negatively charged electrode and buffer at pH 1.68 was added to the water in the electrolyte cell until the pH reached approximately 2, to ensure an adequate supply of $H^+$ ions.

Ten grams of polyvinylpyrrolidone were dissolved in Milli-Q water to prepare a 100 mL polyvinylpyrrolidone solution. The hydrogenated palladium granules were rinsed with Milli-Q water, added to the polyvinylpyrrolidone solution, and stirred for four days. The palladium granules were then removed from the polyvinylpyrrolidone solution by filtering through a 0.2 μm filter, the polyvinylpyrrolidone solution was lyophilized, and the solid polyvinylpyrrolidone was tested for peroxide content.

As shown in Table 16 below, after treatment with palladium granules for four days, the peroxide content of the polyvinylpyrrolidone was reduced from 353.97 ppm to 50.31 ppm.

Comparison of the Effectiveness of Palladium Granules and Palladium Black on Peroxide Removal from Polyvinylpyrrolidone.

The following experiments were preformed to compare the effectiveness of palladium granules and palladium black under various conditions for the removal of peroxide from polyvinylpyrrolidone. One lot of 5 g of palladium granules and three lots of 5 g of palladium black were hydrogenated using an electrolyte cell similar to that shown in FIG. 6, with the exception that instead of a platinum wire, platinum foil was used for the positive and negative electrodes. Each palladium lot was hydrogenated for 2 days.

Polyvinylpyrrolidone was dissolved in Milli-Q water to prepare a 10% (w/v) polyvinylpyrrolidone solution, and each lot of the hydrogenated palladium was rinsed with Milli-Q water and added to separate batches of the polyvinylpyrrolidone solution. As shown in Table 9, hydrogen gas ($H_2$) from a hydrogen generator was bubbled into the polyvinylpyrrolidone solution containing the palladium granules and into one of the polyvinylpyrrolidone solutions containing the palladium black. The temperature of another of the polyvinylpyrrolidone solutions containing the palladium black was increased to 45° C. The experiments in which hydrogen gas was bubbled into the polyvinylpyrrolidone solution and in which the temperature was increased to 45° C. were performed in a fume hood. Samples were taken from the polyvinylpyrrolidone/palladium solutions after the first 2 hours and periodically thereafter. All samples were filtered through a 0.2 μm filter, lyophilized, and the solid polyvinylpyrrolidone was tested for peroxides.

TABLE 9

Comparison of the effectiveness of palladium granules and palladium black

| Pd treated lot # | Pd form | Hydrogen bubbling (Y/N) | Temperature | Experimental data location |
|---|---|---|---|---|
| 1. | Granules | Y | Room | Table 10 |
| 2. | Black | Y | Room | Table 11 |
| 3. | Black | N | Room | Table 12 |
| 4. | Black | N | 45° C. | Table 13 |

As shown in Table 10, palladium granules treated with hydrogen gas for 2 hours reduced the level of peroxides in the polyvinylpyrrolidone to 277.82 ppm; palladium granules treated with hydrogen gas for 26.42 hours reduced the level of peroxides in the polyvinylpyrrolidone to 217.36 ppm; and palladium granules treated with hydrogen gas for 99.33 hours reduced the level of peroxides in the polyvinylpyrrolidone to 79.12 ppm.

TABLE 10

Palladium granules treated with hydrogen gas

| | Time (h) | | | | | | | |
|---|---|---|---|---|---|---|---|---|
| | 0.00 | 2.00 | 18.33 | 26.42 | 43.92 | 66.33 | 90.33 | 99.33 |
| Average, ppm | 375.87 | 277.82 | 232.74 | 217.36 | 131.28 | 103.69 | 76.17 | 79.12 |
| StdDev | 41.76 | 0.45 | 0.86 | 0.24 | 0.45 | 0.42 | 19.72 | 0.32 |

As shown in Table 11, palladium black treated with hydrogen gas for 2 hours reduced the level of peroxides in the polyvinylpyrrolidone to 15.46 ppm; palladium black treated with hydrogen gas for 26.25 hours reduced the level of peroxides in the polyvinylpyrrolidone to 4.95 ppm; and palladium black treated with hydrogen gas for 98.92 hours reduced the level of peroxides in the polyvinylpyrrolidone to 3.12 ppm.

TABLE 11

Palladium black treated with hydrogen gas

| | Time (h) | | | | | | | |
|---|---|---|---|---|---|---|---|---|
| | 0.00 | 2.00 | 18.25 | 26.25 | 43.92 | 66.00 | 90.00 | 98.92 |
| Average, ppm | 389.14 | 15.46 | 5.82 | 4.95 | 4.54 | 3.95 | 4.08 | 3.12 |
| StdDev | 4.72 | 1.83 | 1.02 | 0.06 | 0.37 | 0.04 | 0.14 | 0.34 |

As shown in Table 12, palladium black at room temperature reduced the level of peroxides in the polyvinylpyrrolidone to 19.60 ppm after 2 hours; to 3.72 ppm after 26 hours; and to 0.77 ppm after 68.42 hours.

TABLE 12

Palladium black at room temperature

| | Time (h) | | | | | |
|---|---|---|---|---|---|---|
| | 0.00 | 2.00 | 4.25 | 20.50 | 26.00 | 44.42 | 68.42 |
| Average, ppm | 464.67 | 19.60 | 12.64 | 3.88 | 3.72 | 2.07 | 0.77 |
| StdDev | 11.61 | 0.24 | 0.20 | 0.04 | 0.34 | 0.13 | 0.02 |

As shown in Table 13, palladium black at 45° C. reduced the level of peroxides in the polyvinylpyrrolidone to 23.40 ppm after 2 hours; to 19.87 ppm after 4 hours; to 18.91 ppm after 5.75 hours; to 9.96 ppm after 8 hours; and to 2.62 ppm after 31 hours.

TABLE 13

Palladium black at 45° C.

| | Time (h) | | | | | |
|---|---|---|---|---|---|---|
| | 0.00 | 2.00 | 4.00 | 5.75 | 8.00 | 31.00 |
| Average, ppm | 293.47 | 23.40 | 19.87 | 18.91 | 9.96 | 2.62 |
| StdDev | 41.18 | 1.24 | 7.60 | 1.78 | 0.38 | 1.09 |

Optimization of the Ratio of Polyvinylpyrrolidone to Palladium Black

Experiments were performed to optimize the amount of palladium black needed for removal of peroxide from polyvinylpyrrolidone.

Each of three lots of 5 g of palladium black was hydrogenated for 2 days using the procedure described above in which platinum foil was used for the positive and negative electrodes of the electrolyte cell. Following hydrogenation, three 10% (w/v) solutions of polyvinylpyrrolidone were prepared as shown in Table 14. The hydrogenated palladium black was rinsed with Milli-Q water, added to the polyvinylpyrrolidone solutions, and the mixtures were stirred for 24 hours with sampling at 1 h, 3 h, 5 h, 7 h, 22 h and 24 h. Each polyvinylpyrrolidone sample was filtered through a 0.2 μm filter, lyophilized, and the solid polyvinylpyrrolidone was tested for peroxides.

TABLE 14

Optimization of the ratio of polyvinylpyrrolidone to palladium black

| Pd treated lot # | PVP amount, g | 10% PVP water solution volume, mL |
|---|---|---|
| 1 | 2.5 | 25 |
| 2 | 5 | 50 |
| 3 | 10 | 100 |

As shown in Table 15, treatment with an excess of palladium black for 24 hours was required to reduce peroxide levels to approximately 1 ppm.

TABLE 15

Optimization of the ratio of polyvinylpyrrolidone to palladium black

| | Time (h) | | | | | | |
|---|---|---|---|---|---|---|---|
| | 0.00 | 1.00 | 3.00 | 5.00 | 7.00 | 22.00 | 24.00 |
| PVP:Pd = 1:2 | 427.70 | 7.50 | 4.46 | 3.53 | 3.12 | 1.46 | 1.14 |
| PVP:Pd = 1:1 | 427.70 | 37.62 | 20.75 | 17.44 | 11.27 | 7.52 | 3.62 |
| PVP:Pd = 0.5:1 | 427.70 | 62.89 | 37.03 | 28.52 | 23.10 | 15.52 | 11.21 |

The Use of Alumina for the Removal of Peroxides

Ten grams of polyvinylpyrrolidone were dissolved in Milli-Q water to prepare a 100 mL solution of polyvinylpyrrolidone. Ten grams of alumina were added to the polyvinylpyrrolidone solution and the mixture was stirred for 4 days, at which time the alumina was allowed to settle to the bottom of the solution. The solution was filtered through a 0.2 μm filter, lyophilized, and the solid polyvinylpyrrolidone was tested for peroxides.

As shown in Table 16 below, after treatment with alumina for four days, the peroxide content of the polyvinylpyrrolidone was reduce from 353.97 ppm to 215.24 ppm.

The Use of Ammonia for the Removal of Peroxides

Ten grams of polyvinylpyrrolidone were dissolved in Milli-Q water to prepare a 100 mL polyvinylpyrrolidone solution. Ammonia ($NH_4OH$) was added to the polyvinylpyrrolidone solution dropwise until the pH of the solution was between 8 and 9. The solution was then stirred for 4 days at room temperature. The pH of the solution was checked periodically and additional ammonia was added to the solution as needed to maintain the pH. The solution was lyophilized and the solid polyvinylpyrrolidone was tested for peroxides.

As shown in Table 16, after treatment with ammonia for four days, the peroxide content of the polyvinylpyrrolidone was reduced from 353.97 ppm to 118.89 ppm.

Figure 7:
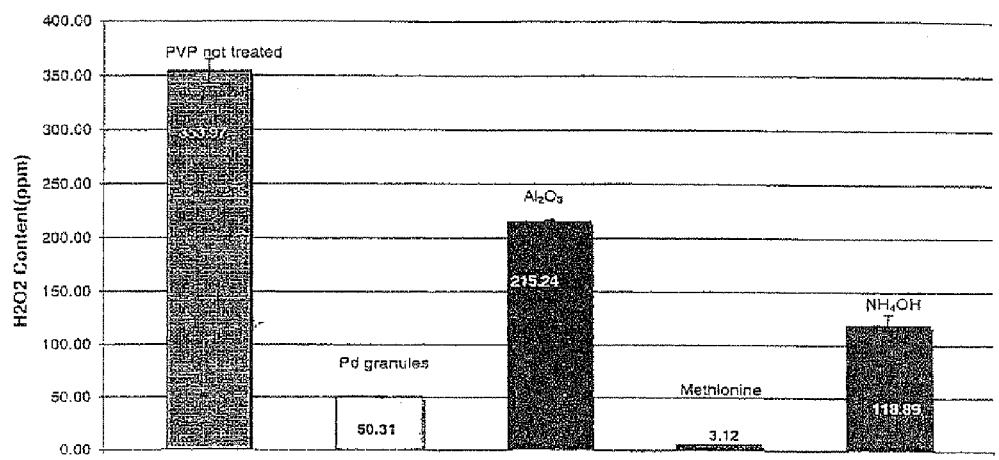
FIG. 7 depicts the results of experiments in which the efficacy of palladium, aluminum oxide (alumina), methionine, and ammonia for removing peroxide from polyvinylpyrrolidone was compared.

Results of the Comparison of Various Means for the Removal of Peroxide from Polyvinylpyrrolidone As shown in Table 16 and FIG. 7, treatment with methionine was the most effective means for the removal of peroxide from polyvinylpyrrolidone as compared to treatment with palladium, alumina, or ammonia.

TABLE 16

Comparison of various means for removal of peroxide from polyvinylpyrrolidone.

| Method of treatment | $H_2O_2$ content, ppm (avg.) | Note |
|---|---|---|
| PVP not treated | 353.97 | N/A |
| 10% DL-Methionine | 3.12 | N/A |

TABLE 16-continued

Comparison of various means for removal of peroxide from polyvinylpyrrolidone.

| Method of treatment | $H_2O_2$ content, ppm (avg.) | Note |
|---|---|---|
| $NH_4OH$ (pH control method) | 118.89 | After 4 days treatment |
| Pd granules | 50.31 | After 4 days treatment |
| $Al_2O_3$ | 215.24 | After 4 days treatment |

Example 9

The Effect of Peroxides on Omega-IFN Stability in a Benzyl Alcohol/Polyvinylpyrrolidone Vehicle The experiments described below were performed to determine whether peroxide levels increase in a benzyl alcohol/polyvinylpyrrolidone vehicle over time, and to investigate the sensitivity of omega-IFN stability to the peroxide content of a benzyl alcohol/polyvinylpyrrolidone vehicle.

Preparation of Benzyl Alcohol/Polyvinylpyrrolidone Formulations

Five benzyl alcohol/polyvinylpyrrolidone formulations (40% benzyl alcohol and 60% polyvinylpyrrolidone) were prepared that contained different levels of peroxide. Benzyl alcohol was treated to lower peroxide content. The polyvinylpyrrolidone was fully and partially treated for peroxides with L-methionine, which is described in more detail below. Preparations containing a range of peroxide levels were prepared by blending treated benzyl alcohol with untreated benzyl alcohol and mixing such preparations with the fully and partially treated polyvinylpyrrolidone preparations.

All procedures were preformed inside a nitrogen dry box with the exception of the peroxide removal from polyvinylpyrrolidone procedure, which was preformed on the open bench top.

Benzyl Alcohol Preparation

Benzyl alcohol was treated to lower the peroxide level. Untreated and treated benzyl alcohol were tested for peroxide content (see Table 18) and a mid range benzyl alcohol peroxide level for vehicle four was set to 5.5 ppm (48% untreated benzyl alcohol and 52% treated benzyl alcohol).

Blending both benzyl alcohol batches were performed as described below in a nitrogen dry box under the following conditions:

Dry box temperature: 25° C.
Dew point: −60° C.
Oxygen level: 129 ppm

The calculated amount of untreated benzyl alcohol was weighed in a small amber glass vial and the calculated amount of treated benzyl alcohol was added to it. A stir bar was added to the vial and the vial was placed on a magnetic stir plate and stirred for 10 minutes. Samples were taken for peroxide content testing (see Table 18).

Removal of Peroxides from Polyvinylpyrrolidone

Approximately 200 g of polyvinylpyrrolidone were treated for peroxides with L-methionine. The polyvinylpyrrolidone was weighed into a beaker, transferred into a glass bottle with a lid and stir bar, and placed on a magnetic stir plate. Milli-Q water was added to the bottle to a total volume of 2 L and the solution was stirred until the polyvinylpyrrolidone was completely dissolved. Approximately 20 g (10%) of L-methionine were weighed on a weigh boat and carefully transferred to the bottle while stirring. The solution was stirred overnight and filtered through a 0.2 µm Nalgene filter. The L-methionine was removed from the polyvinylpyrrolidone solution by diafiltration through the Millipore TFF diafiltration system and Milli-Q water was used as the diafiltration media. Diafiltration was performed until 15 L of water had passed through the polyvinylpyrrolidone solution. The solution was filtered through a 0.2 µm Nalgene filter, dispensed in 10 mL labeled lyophilizing vials with stoppers, and lyophilized. The lyophilizing process parameters are shown in Table 17.

TABLE 17

Lyophilizing process parameters

| | | Shelf conditions | | Condenser conditions | | |
|---|---|---|---|---|---|---|
| Time Min | Ramping ° C./min | Target temperature ° C. | Pressure relative to absolute vacuum* mT | Target temperature ° C. | Foreline pressure* mT | Note |
| 60 | −2.5 | −50 | N/A | N/A | N/A | Freezing |
| 120 | N/A | −50 | N/A | N/A | N/A | Holding |
| N/A | N/A | −50 | N/A | −40 | N/A | Switching on the condenser |
| N/A | N/A | −50 | ≦150 | ≦−40 | ≦100 | Starting the vacuum pump |
| ≧5100 | +0.16 | 40 | ≦200 | ≦−40 | ≦100 | Drying |

*The pressure was created by a vacuum pump and the numbers in the table represent absolute pressure relative to the absolute zero.

After the lyophilization was complete the samples were assayed for peroxide content and for residual L-methionine content (see Table 18). The residual L-methionine in the polyvinylpyrrolidone preparation was 3.2 ppm for the fully treated sample and 0.4 ppm for the partially treated sample.

The same procedure as described above was followed for the partial peroxide treatment of polyvinylpyrrolidone with the only difference being that 2 g (1%) of L-methionine were used instead of 20 g.

Preparation of Benzyl Alcohol/Polyvinylpyrrolidone Vehicles Containing Various Peroxide Contents The benzyl alcohol and polyvinylpyrrolidone preparations were tested for peroxides after the peroxide removal treatment. Five preparations with a range of peroxide levels were prepared by blending treated benzyl alcohol with untreated benzyl alcohol and mixing the blends with the fully and partially L-methionine treated polyvinylpyrrolidone preparations. Table 18 illustrates the peroxide content of each of the five benzyl alcohol/polyvinylpyrrolidone preparations.

TABLE 18

Peroxide content for vehicles

| Vehicle ID | Benzyl Alcohol | | PVP | | Vehicle peroxide content measured, ppm |
| --- | --- | --- | --- | --- | --- |
| | Treatment | Peroxide content, ppm | Treatment | Peroxide content, ppm | |
| 1 | No | 10.94 ± 1.14 | Partial | 8.52 ± 0.93 | 10.73 ± 0.54 |
| 2 | No | 10.94 ± 1.14 | Full | 1.27 ± 0.11 | 5.90 ± 0.47 |
| 3 | Yes | 0.56 ± 0.24 | Full | 1.27 ± 0.11 | 3.53 ± 0.16 |
| 4 | Blend | 4.42 ± 0.15 | Full | 1.27 ± 0.11 | 4.42 ± 0.34 |
| 5 | Yes | 0.56 ± 0.24 | Partial | 8.52 ± 0.93 | 8.59 ± 1.35 |

All vehicles were tested for moisture content and showed very low moisture levels as presented in Table 19 below. The initial peroxide levels of the vehicles were determined at the time of mixing to compare the actual values with the calculated values, and were also tested at t=0 after receiving the same treatment as described below for the corresponding suspensions (refrigeration after sampling).

TABLE 19

Vehicle peroxide and moisture content

| Vehicle ID | Vehicle initial peroxide content after mixing ppm | Vehicle peroxide content at t = 0 ppm | Moisture content % |
| --- | --- | --- | --- |
| 3 | 3.53 | 2.73 | 0.04 |
| 4 | 4.42 | 3.00 | 0.04 |
| 2 | 5.90 | 5.08 | 0.05 |
| 5 | 8.59 | 7.75 | 0.05 |
| 1 | 10.73 | 10.84 | 0.05 |

Preparation of Benzyl Alcohol/Polyvinylpyrrolidone Vehicles

Five 20 g vehicle batches were mixed inside the dry box under the following conditions and according to the procedure described below:

Dry box temperature: 26° C.-27° C.

Dew point: −60° C.-−57° C.

Oxygen level: 94 ppm-205 ppm

Approximately 8 g of benzyl alcohol were weighed in a glass crystallizing vial (50×70 mm) and put on a hot plate. The temperature on the surface of the hot plate was 50° C. Approximately 12 g of polyvinylpyrrolidone were weighed in a weigh boat and slowly added to the benzyl alcohol while mixing with a spatula. Mixing was continued until the polyvinylpyrrolidone was fully dissolved in the benzyl alcohol and clear gels were formed. Mixing was stopped occasionally and the mixing vial was covered with a petri dish while on the hot plate to allow air bubble clearing and visual examination of the gel. The vehicle was transferred to a pre-weighed jar and sampled for moisture content and peroxide content tests. The jar was covered, put in a foil pouch, removed from the dry box and immediately sealed.

Sample Preparation

Five 4 g suspension batches were mixed inside the dry box under the following conditions and according to the procedures described below:

Dry box temperature: 26° C.-27° C.

Dew point: −68° C.-−72° C.

Oxygen level: 27 ppm-100 ppm

For each suspension, 3.6 g of the vehicle were weighed in a glass vial. Then 0.4 g of the particle formulation (Interferon/Sucrose/L-Methionine/Citrate) were weighed on top of the vehicle and the vial was placed on a hot plate. The temperature on the surface of the hot plate was maintained at around 50° C. and was periodically checked with a thermocouple thermometer. The particles were carefully incorporated in the vehicle by spatula and then mixed for 15 minutes. Samples were prepared from the suspensions.

For each formulation, 56 lyophilizing vials (5 mL) were labeled: 24 for the suspension samples and 32 for the vehicle samples. Suspension samples of ~144 mg were put on the bottom of 24 of the vials and the net weight of each vial was taken. The vials were stopped with Teflon coated rubber stoppers and sealed with metal seals. 32 samples of vehicle only were prepared following the procedure used for the suspension samples.

Stability Study

For each vehicle, two sets of samples were prepared in the dry box: one set with omega-IFN particles and another one without omega-IFN particles. Samples containing protein had a protein concentration of 1.73% (10% particle loading). For assay quantitation purposes, the omega-IFN content in each sample had to be at least 2.5 mg. Sample vials were sealed under nitrogen and protected from light by heat-sealing in poly-foil pouches.

Samples of each vehicle with protein and without protein were incubated at 40° C. to simulate the worst-case body temperature and at 65° C. to compare short-term stability results at 65° C. with longer-term stability results at 40° C.

9). The absolute peroxide content for all the vehicles incubated at 65° C. for 14 days differed substantially from the absolute peroxide content of the corresponding vehicles incubated at 40° C. for three months.

TABLE 20

Stability of peroxides in benzyl alcohol/polyvinylpyrrolidone vehicle at 40° C. and 65° C.

| Temperature conditions | Time point | Peroxide content in vehicles (n = 3), ppm. ("±" range represents StDev) | | | | |
|---|---|---|---|---|---|---|
| | | 3 | 4 | 2 | 5 | 1 |
| N/A | t = 0 | 2.73 ± 0.17 | 3.00 ± 0.15 | 5.08 ± 0.23 | 7.75 ± 0.29 | 10.84 ± 0.29 |
| 40° C. | t = 1 week | 2.94 ± 0.17 | 3.26 ± 0.14 | 6.62 ± 1.9 | 8.08 ± 0.54 | 10.61 ± 0.21 |
| | t = 2 weeks | 2.67 ± 0.32 | 3.11 ± 0.34 | 4.31 ± 0.12 | 7.07 ± 0.60 | 8.77 ± 0.43 |
| | t = 1 month | 3.46 ± 0.21 | 3.78 ± 0.27 | 5.23 ± 0.12 | 7.74 ± 0.22 | 9.90 ± 0.38 |
| | t = 1.5 months | 4.34 ± 0.40 | 4.49 ± 0.14 | 6.16 ± 0.39 | 9.46 ± 0.33 | 10.48 ± 0.17 |
| | t = 3 months | 8.14 ± 0.66 | 8.24 ± 1.00 | 9.73 ± 0.69 | 12.44 ± 0.37 | 14.96 ± 0.80 |
| 65° C. | t = 1 week | 3.58 ± 0.21 | 2.76 ± 0.11 | 3.69 ± 0.86 | 4.62 ± 0.37 | 5.67 ± 1.75 |
| | t = 2 weeks | 6.12 ± 0.13 | 6.19 ± 0.19 | 6.95 ± 0.34 | 6.83 ± 0.68 | 7.32 ± 0.27 |

Duplicate samples incubated at both 40° C. and 65° C. were tested for protein stability and content at 7 and 14 days, and triplicate samples incubated at 40° C. were tested at 1.5 and 3 months. The time zero stability data was excluded from the final data analyses due to very high oxidation of all samples (~20%), which was highly inconsistent with the data obtained at all other time points. Peroxide testing on vehicles incubated at 40° C. and 65° C. was performed on triplicate samples at time zero, 7 days, and 14 days, and was also performed on vehicles incubated at 40° C. for 1, 2 and 3 months.

The samples containing protein were tested for protein purity and assessed for oxidation and deamidation via reverse-phase high performance liquid chromatography (RP-HPLC), and were tested via size exclusion high performance liquid chromatography (SEC-HPLC) to assess protein precipitation. Samples without protein were tested for peroxide content.

Results

Stability of Peroxides

Figure 8:
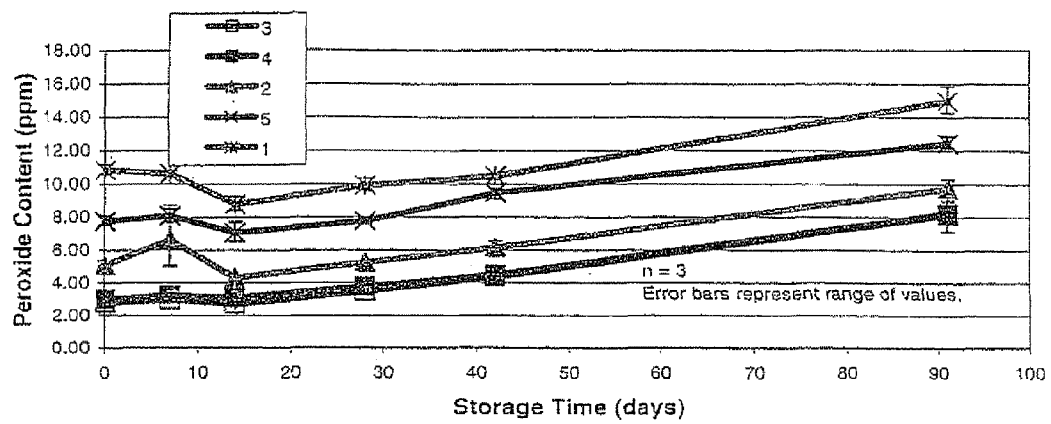
FIG. 8 depicts the peroxide content of various benzyl alcohol/polyvinylpyrrolidone vehicles incubated at 40° C. over a period of 90 days.
Figure 9:
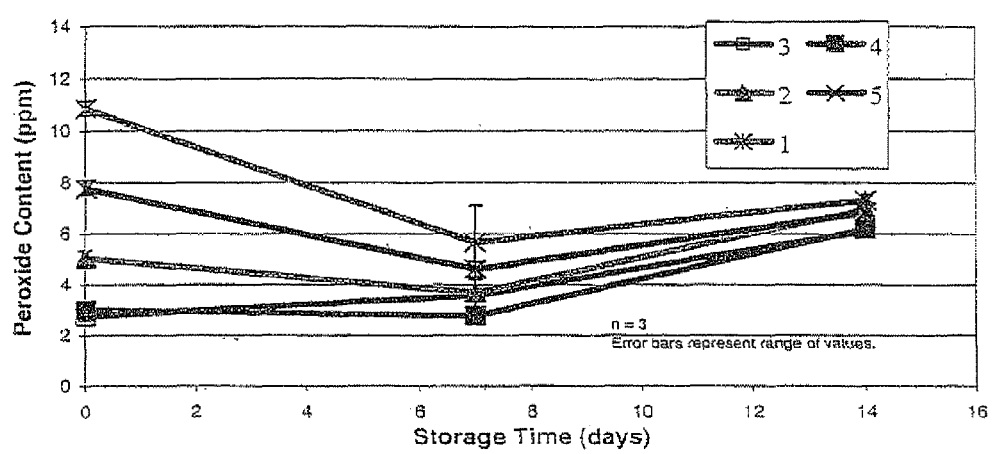
FIG. 9 depicts the peroxide content of various benzyl alcohol/polyvinylpyrrolidone vehicles incubated at 65° C. over a period of 14 days.

The peroxide content of the benzyl alcohol/polyvinylpyrrolidone vehicles incubated at 40° C. increased over a period of 3 months (Table 20 and FIG. 8). The increase was greater for vehicles containing lower initial peroxide levels (~200%) and was lower for vehicles containing higher initial peroxide levels (~38%), but was in the range of 4-6 ppm for all vehicles tested.

For vehicles 2, 3, and 4, the increase in the peroxide levels after 14 days at 65° C. was greater than that of the corresponding vehicles incubated 14 days at 40° C. (Table 20 and FIG.

Peroxide levels in the benzyl alcohol/polyvinylpyrrolidone vehicles at time zero and after incubation at 40° C. for three months were analyzed statistically using JMP® software (SAS Institute) by modeling the peroxide content as a function of the initial peroxide levels in the raw materials (benzyl alcohol and polyvinylpyrrolidone). As shown in Table 21, changes in the peroxide content of polyvinylpyrrolidone resulted in an impact on the vehicle peroxide content that was three times greater than the impact caused by changes in the benzyl alcohol peroxide content.

TABLE 21

Summary of model fit and parameter estimate results for peroxide content in vehicles as a function of the initial peroxide content in the benzyl alcohol and polyvinylpyrrolidone.

| Parameters | t = 0 | t = 3 months |
|---|---|---|
| RSquare | 0.994 | 0.989 |
| RSquare Adjusted | 0.988 | 0.979 |
| Mean of Response | 5.88 | 10.68 |
| Observations | 5 | 5 |
| Parameter estimate for PVP initial peroxide content | 0.775 (p = 0.0039) | 0.686 (p = 0.0063) |
| Parameter estimate for BA initial peroxide content | 0.266 (p = 0.0186) | 0.207 (p = 0.0380) |

Omega-IFN Oxidation

Figure 10:
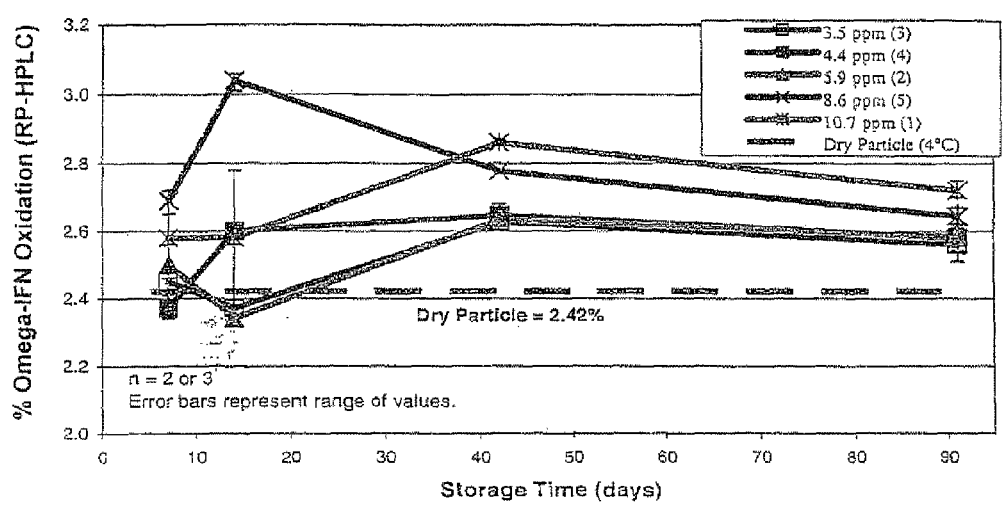
FIG. 10 depicts the degree of oxidation of omega-IFN incubated at 40° C. over a period of 90 days in benzyl alcohol/polyvinylpyrrolidone vehicles that contained varying levels of peroxide.
Figure 11:
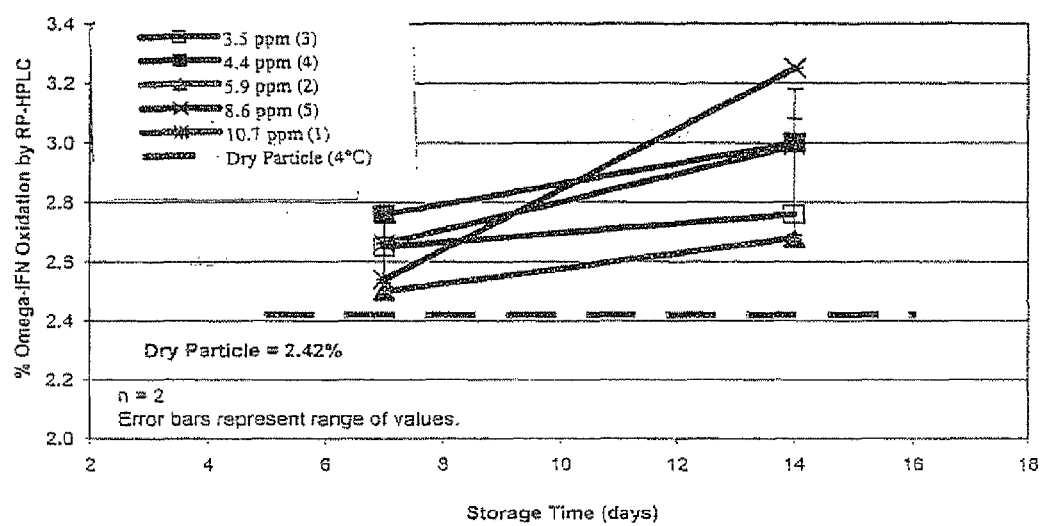
FIG. 11 depicts the degree of oxidation of omega-IFN incubated at 65° C. over a period of 14 days in benzyl alcohol/polyvinylpyrrolidone vehicles that contained varying levels of peroxide.

As shown in Table 22 and FIG. 10, oxidation of omega-IFN samples incubated at 40° C. for 7 days to 1.5 months and containing a range of vehicle peroxide contents did not differ substantially between the various formulations, and was in the range of 2.34% to 3.04%. At 3 months, the level of protein oxidation for all the vehicles tested ranged from 2.56% to 2.72%. The samples incubated at 65° C. exhibited higher oxidation of omega-IFN as compared to samples incubated at 40° C. (FIGS. 10 and 11).

TABLE 22

Omega-IFN oxidation for a range of peroxide contents - benzyl alcohol/polyvinylpyrrolidone suspensions incubated at 40° C. & 65° C.

| | | omega-IFN Oxidation, %. ("±" range represents StDev) | | | | |
|---|---|---|---|---|---|---|
| Temperature conditions | Timepoint | 3 (2.73 ppm) | 4 (3.00 ppm) | 2 (5.08 ppm) | 5 (7.75 ppm) | 1 (10.84 ppm) |
| 40° C. | t = 1 week, n = 2 | 2.45 ± 0.16 | 2.37 ± 0.02 | 2.50 ± 0.12 | 2.69 ± 0.05 | 2.58 ± 0.17 |
| | t = 2 weeks, n = 2 | 2.37 ± 0.07 | 2.60 ± 0.25 | 2.34 ± 0.01 | 3.04 ± 0.04 | 2.58 ± 0.3 |
| | t = 1.5 months, n = 3 | 2.63 ± 0.01 | 2.65 ± 0.03 | 2.63 ± 0.02 | 2.78 ± 0.01 | 2.86 ± 0.01 |
| | t = 3 months, n = 3 | 2.56 ± 0.02 | 2.58 ± 0.03 | 2.58 ± 0.09 | 2.64 ± 0.03 | 2.72 ± 0.03 |
| 65° C. | t = 1 week, n = 2 | 2.62 ± 0.18 | 2.76 ± 0.00 | 2.50 ± 0.01 | 2.54 ± 0.01 | 2.66 ± 0.01 |
| | t = 2 weeks, n = 2 | 2.76 ± 0.10 | 3.00 ± 0.25 | 2.68 ± 0.04 | 3.25 ± 0.00 | 2.99 ± 0.13 |

As shown in FIG. 10, the level of oxidation of omega-IFN for samples incubated at 40° C. for three months was comparable to that observed after incubation at 40° C. for just 7 days. In addition, the various peroxide levels had little effect on the level of omega-IFN oxidation.

Omega-IFN Deamidation

Figure 13:
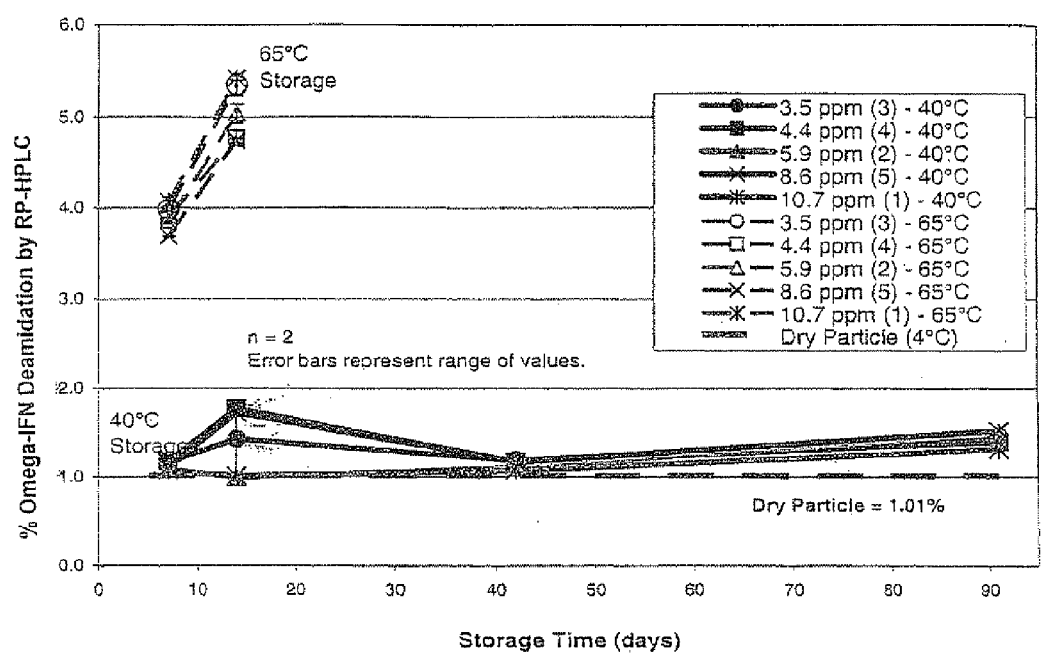
FIG. 13 depicts the degree of deamidation of omega-IFN incubated at 40° C. for 90 days or at 65° C. for 14 days in benzyl alcohol/polyvinylpyrrolidone vehicles that contained varying levels of peroxide.

As shown in Table 23 and FIG. 13, there was no substantial change in the degree of omega-IFN deamidation after incubation of the vehicles for 3 months at 40° C. The level of peroxide therefore did not appear to affect the degree of deamidation. For all the vehicles tested, the level of omega-IFN deamidation was in the range of 0.99% to 1.72%.

The level of deamidation increased for vehicles incubated 14 days at 65° C. and was in the range of 3.69% to 5.42%.

Omega-IFN Aggregation

Figure 14:
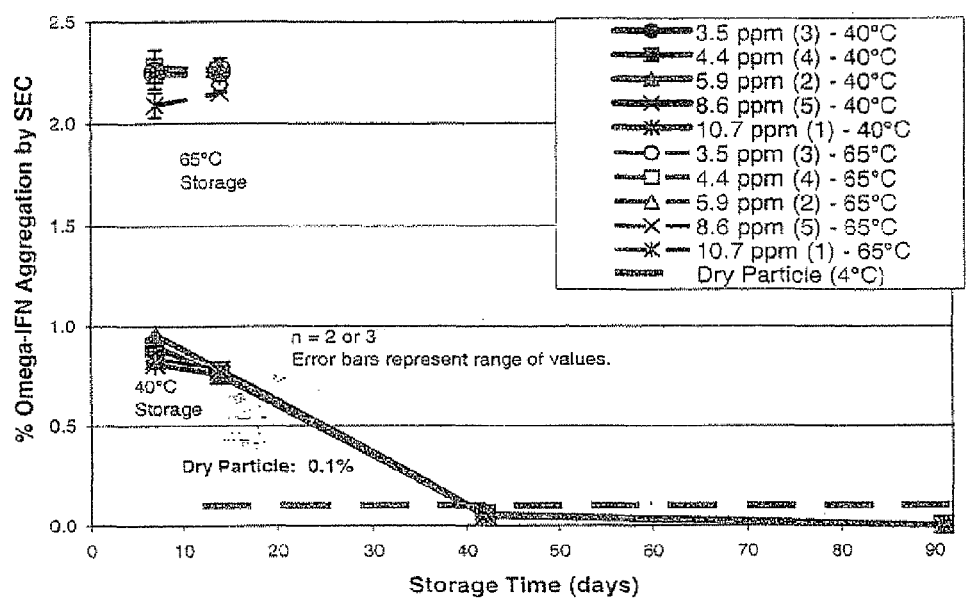
FIG. 14 depicts the degree of aggregation of omega-IFN incubated at 40° C. for 90 days or at 65° C. for 14 days in benzyl alcohol/polyvinylpyrrolidone vehicles that contained varying levels of peroxide.

As shown in Table 24 and FIG. 14, the degree of aggregation of omega-IFN decreased over time for samples incubated at 40° C., but the level of peroxide did not appear to affect the degree of aggregation. Samples incubated at 65° C. showed substantially higher aggregation than did samples incubated at 40° C.

TABLE 23

Omega-IFN deamidation for a range of peroxide contents - benzyl alcohol/polyvinylpyrrolidone suspensions incubated at 40° C. & 65° C.

| | | omega-IFN Deamidation, % ("±" range represents StDev) | | | | |
|---|---|---|---|---|---|---|
| Temperature conditions | Timepoint | 3 (2.73 ppm) | 4 (3.00 ppm) | 2 (5.08 ppm) | 5 (7.75 ppm) | 1 (10.84 ppm) |
| 40° C. | t = 1 week, n = 2 | 1.17 ± 0.06 | 1.17 ± 0.05 | 1.08 ± 0.02 | 1.10 ± 0.01 | 1.06 ± 0.01 |
| | t = 2 weeks, n = 2 | 1.42 ± 0.57 | 1.77 ± 0.03 | 0.99 ± 0.04 | 1.72 ± 0.04 | 1.01 ± 0.09 |
| | t = 1.5 months, n = 3 | 1.19 ± 0.02 | 1.17 ± 0.01 | 1.10 ± 0.03 | 1.17 ± 0.02 | 1.07 ± 0.02 |
| | t = 3 months, n = 3 | 1.45 ± 0.17 | 1.39 ± 0.06 | 1.50 ± 0.09 | 1.52 ± 0.05 | 1.31 ± 0.13 |
| 65° C. | t = 1 week, n = 2 | 3.98 ± 0.04 | 3.90 ± 0.09 | 3.86 ± 0.02 | 3.69 ± 0.01 | 4.07 ± 0.06 |
| | t = 2 weeks, n = 2 | 5.35 ± 0.17 | 4.77 ± 0.12 | 5.04 ± 0.15 | 4.74 ± 0.04 | 5.42 ± 0.03 |

TABLE 24

Omega-IFN aggregation for a range of peroxide contents - benzyl alcohol/
polyvinylpyrrolidone suspensions incubated at 40° C. & 65° C.

| Temperature conditions | Timepoint | omega-IFN Aggregation, % ("±" range represents StDev) | | | | |
|---|---|---|---|---|---|---|
| | | 3 (2.73 ppm) | 4 (3.00 ppm) | 2 (5.08 ppm) | 5 (7.75 ppm) | 1 (10.84 ppm) |
| 40° C. | t = 1 week, n = 2 | 0.83 ± 0.01 | 0.90 ± 0.01 | 0.96 ± 0.03 | 0.83 ± 0.04 | 0.81 ± 0.06 |
| | t = 2 weeks, n = 2 | 0.75 ± 0.03 | 0.75 ± 0.03 | 0.78 ± 0.01 | 0.78 ± 0.06 | 0.76 ± 0.04 |
| | t = 1.5 months, n = 3 | 0.05 ± 0.00* | 0.06 ± 0.01* | 0.05 ± 0.00* | 0.05 ± 0.01* | 0.06 ± 0.01* |
| | t = 3 months, n = 3 | Trace | Trace | Trace | Trace | Trace |
| 65° C. | t = 1 week, n = 2 | 2.25 ± 0.06 | 2.28 ± 0.08 | 2.27 ± 0.13 | 2.09 ± 0.08 | 2.24 ± 0.01 |
| | t = 2 weeks, n = 2 | 2.26 ± 0.01 | 2.26 ± 0.01 | 2.27 ± 0.06 | 2.15 ± 0.01 | 2.23 ± 0.04 |

*Dimer only, no high aggregate registered.

Omega-IFN Recovery

Figure 12:
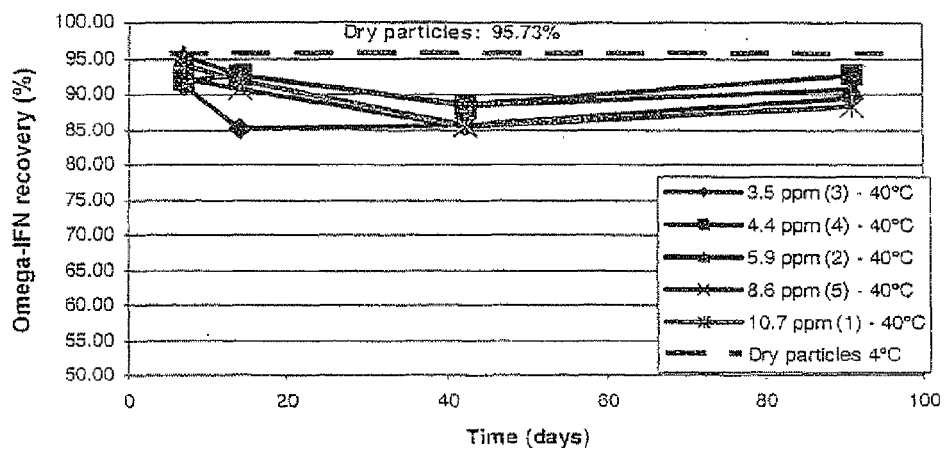
FIG. 12 depicts the recovery of omega-IFN incubated at 40° C. for either 7 days or three months in benzyl alcohol/polyvinylpyrrolidone vehicles that contained varying levels of peroxide.

As shown in Table 25 and FIG. 12, 85.21% to 95.37% of the omega-IFN was recovered for all the vehicles incubated at both temperatures and did not show a substantial change over time.

TABLE 25

Omega-IFN recovery for a range of peroxide contents - benzyl alcohol/
polyvinylpyrrolidone suspensions incubated at 40° C. & 65° C.

| Temperature conditions | Timepoint | omega-IFN Recovery, %, ("±" range represents StDev) | | | | |
|---|---|---|---|---|---|---|
| | | 3 (2.73 ppm) | 4 (3.00 ppm) | 2 (5.08 ppm) | 5 (7.75 ppm) | 1 (10.84 ppm) |
| 40° C. | t = 1 week, n = 2 | 91.31 ± 0.43 | 91.83 ± 0.62 | 95.37 ± 0.74 | 92.17 ± 1.98 | 94.15 ± 1.32 |
| | t = 2 weeks, n = 2 | 85.21 ± 6.46 | 92.67 ± 1.03 | 92.78 ± 1.33 | 90.83 ± 1.42 | 91.91 ± 0.43 |
| | t = 1.5 months, n = 3 | 85.54 ± 0.83 | 88.59 ± 0.10 | 88.21 ± 1.07 | 85.48 ± 1.11 | 85.55 ± 0.91 |
| | t = 3 months, n = 3 | 89.59 ± 4.79 | 92.74 ± 0.67 | 90.62 ± 1.77 | 90.28 ± 3.07 | 88.30 ± 4.72 |
| 65° C. | t = 1 week, n = 2 | 92.09 ± 2.31 | 88.52 ± 5.09 | 93.91 ± 1.14 | 93.05 ± 0.49 | 92.48 ± 2.16 |
| | t = 2 weeks, n = 2 | 89.49 ± 0.67 | 92.00 ± 0.58 | 91.21 ± 0.42 | 90.04 ± 0.01 | 92.11 ± 0.72 |

It is to be appreciated that certain features of the invention which are, for clarity, described above in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

The entire disclosure of each patent, patent application, and publication cited or described in this document is incorporated herein by reference.

What is claimed:

1. A method for reducing the level of peroxide present in a biocompatible polymer and forming a drug delivery formulation, said method comprising:
   solubilizing the biocompatible polymer in water to form an aqueous solution, wherein the biocompatible polymer is water soluble;
   combining methionine with the aqueous solution comprising the biocompatible polymer to obtain a polymer preparation having a reduced level of peroxide;
   removing substantially all of the water from the polymer preparation;
   combining the polymer preparation with a solvent to form a drug delivery vehicle solution;
   combining the drug delivery vehicle solution with a drug to form a drug delivery formulation comprising the drug suspended in the drug delivery vehicle solution and wherein the drug delivery formulation is nonaqueous.

2. The method of claim 1, wherein about less than 35% of the drug in the drug delivery formulation is degraded by oxidation, deamidation, and hydrolysis after maintenance of the formulation at 37° C. for a period of two months.

3. The method of claim 1, wherein about less than 15% of the drug in the drug delivery formulation is degraded through aggregation after maintenance of the formulation at 37° C. for a period of two months.

4. The method of claim 1, wherein the drug is a particulate material.

5. The method of claim 1, wherein the drug is medicines, vitamins, nutrients, or food supplements.

6. The method of claim 1, wherein the drug is a peptide or protein.

7. The method of claim 1, wherein the drug is at least one member selected from adrenocorticotropic hormone, angiotensin I, angiotension II, atrial natriuretic peptide, bombesin, bradykinin, calcitonin, cerebellin, dynorphin, alpha endorphin, beta endorphin, endothelin, enkephalin, epidermal growth factor, fertirelin, follicular gonadotropin releasing peptide, galanin, glucagon, glucagon-like-peptide-1 (GLP-1), gonadorelin, gonadotropin, goserelin, growth hormone releasing peptide, histrelin, human growth hormone, insulin, interferons, leuprolide, luteinizing hormone-releasing hormone (LHRH), motilin, nafarelin, neurotensin, oxytocin, relaxin, somatostatin, substance P, tumor necrosis factor, triptorelin, vasopressin, growth hormone, nerve growth factor, blood clotting factors, ribozymes, and antisense oligonucleotides.

8. The method of claim 1, wherein the biocompatible polymer is selected from a polyester, pyrrolidone, ester of unsaturated alcohols, ether of unsaturated alcohols, polyoxyethylenepolyoxypropylene block copolymer, or combinations thereof.

9. The method of claim 1, wherein the solvent is at least one member selected from glycofurol, tetraglycol, n-methylpyrrolidone, glycerol formal, glycerine, and propylene glycol.

10. The method of claim 1, wherein the drug formulation exhibits peroxide levels below 5 ppm.

11. The method of claim 1, further comprising removing the methionine before removing substantially all of the water from the polymer preparation.

12. The method of claim 11, wherein the removing step of methionine comprises diafiltrating.

13. The method of claim 1, wherein removing substantially all of the water from the polymer preparation comprises lyophilizing.

14. The method of claim 1, wherein the polymer is polyvinylpyrrolidone.

15. The method of claim 1, wherein the methionine is L-methionine.

16. The method of claim 1, wherein the drug delivery vehicle solution has a viscosity ranging from about 1000 poise to about 10,000,000 poise.

17. The method of claim 1, wherein the polymer ranges from about 40 wt % to about 80 wt %, based on the drug delivery vehicle solution.

18. The method of claim 1, wherein the solvent ranges from about 20 wt % to about 60 wt %, based on the drug delivery vehicle solution.

19. The method of claim 1, wherein the drug is stable in the drug delivery formulation at 37° C. for at least two months.

* * * * *